United States Patent
Barenburg et al.

(10) Patent No.: US 6,605,454 B2
(45) Date of Patent: *Aug. 12, 2003

(54) MICROFLUIDIC DEVICES WITH MONOLITHIC MICROWAVE INTEGRATED CIRCUITS

(75) Inventors: Barbara Foley Barenburg, Gilbert, AZ (US); Jeremy Burdon, Scottsdale, AZ (US); Yuk-Tong Chan, Scottsdale, AZ (US); Xunhu Dai, Gilbert, AZ (US); Sean Gallagher, Scottsdale, AZ (US); Piotr Grodzinski, Chandler, AZ (US); Robert Marrero, Chandler, AZ (US); Vijay Nair, Mesa, AZ (US); David Rhine, Phoenix, AZ (US); Thomas Smekal, Phoenix, AZ (US)

(73) Assignee: Motorola, Inc., Schaumburg, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/816,512

(22) Filed: Mar. 22, 2001

(65) Prior Publication Data

US 2002/0115201 A1 Aug. 22, 2002

Related U.S. Application Data

(63) Continuation of application No. 09/397,691, filed on Sep. 16, 1999.

(51) Int. Cl.[7] ............... C12N 13/00; H05B 6/80; A61L 2/12

(52) U.S. Cl. ............... 435/173.7; 219/690; 219/691; 219/692; 219/693; 422/22

(58) Field of Search ............... 435/173.7; 219/690, 219/691, 692, 693; 422/22

(56) References Cited

U.S. PATENT DOCUMENTS

| | | |
|---|---|---|
| 4,327,180 A | 4/1982 | Chen |
| 4,582,629 A | 4/1986 | Wolf |
| 4,674,325 A | 6/1987 | Kiyobe et al. |
| 4,865,748 A | 9/1989 | Morse |
| 4,866,231 A | 9/1989 | Schneider |
| 4,891,239 A | 1/1990 | Dudley et al. |
| 5,073,167 A | 12/1991 | Carr et al. |
| 5,191,182 A | 3/1993 | Gelorme et al. |
| 5,252,294 A | 10/1993 | Kroy et al. |
| 5,304,487 A | 4/1994 | Wilding et al. |
| 5,306,887 A | 4/1994 | Smith |
| 5,403,730 A | 4/1995 | Bayer et al. |
| 5,521,360 A | 5/1996 | Johnson et al. |
| 5,635,143 A | 6/1997 | White et al. |

(List continued on next page.)

FOREIGN PATENT DOCUMENTS

| WO | WO 95/15671 A1 | 6/1995 |
|---|---|---|
| WO | WO 00/21659 | 4/2000 |

OTHER PUBLICATIONS

Fujikawa et al., "Kinetics of Escherichia cold Destruction by Microwave Irradiation," Applied and Environmental Microbiology, Mar. 1992, p. 920–24.

(List continued on next page.)

Primary Examiner—Jon P. Weber
(74) Attorney, Agent, or Firm—Douglas W. Gilmore

(57) ABSTRACT

A microwave device has a monolithic microwave integrated circuit (MMIC) disposed therein for applying microwave radiation to a microfluidic structure, such as a chamber, defined in the device. The microwave radiation from the MMIC is useful for heating samples introduced into the microfluidic structure and for effecting lysis of cells in the samples. Microfabrication techniques allow the fabrication of MMICs that perform heating and cell lysing of samples having volumes in the microliter to picoliter range.

10 Claims, 13 Drawing Sheets

U.S. PATENT DOCUMENTS

| | | | |
|---|---|---|---|
| 5,639,423 A | 6/1997 | Northrup et al. |
| 5,690,614 A | 11/1997 | Carr et al. |
| 5,720,927 A | 2/1998 | Cripe et al. |
| 5,782,897 A | 7/1998 | Carr |
| 5,922,591 A | 7/1999 | Anderson et al. |
| 6,043,080 A | 3/2000 | Lipshutz et al. |
| 6,074,827 A | 6/2000 | Nelson et al. |

OTHER PUBLICATIONS

Ghandi, "VLSI Fabrication Principles," Wiley (1983) Chapter 10.

Ishii "Chapter 8: Propagation at Microwave Frequencies," Handbook of Microwave Technology, 2:207–227 (1995).

Lee et al., "A Micro cell lysis device" IEEE the 11th International Workshop on Micro Electro Mechanical System, Heidelberg Germany Jan. 25–29, (1998).

Hurley et al., "Rapid lysis technique for mycobacterial species," 1987, J. Clin. Microbiol. 25:2227–2229.

Grimberg et al., "A simple methods for the preparation of plasmid and chromosomal *E. coli* DNA," 1989, Nucleic Acids Res. 17:8893.

Waters et al., "Microchip device for cell lysis, multiplex PCR amplification, and electrophoretic sizing," 1998, Anal. Chem. 70:158–162.

Whittaker, G. 1998, "Fast and Furious," New Scientist, Feb. 28, 1998, p. 34–37.

Dealler et al., "Superficial microwave heating," 1990, Nature (London) 344:496.

Hultner et al., "A Bacterial plasmid DNA miniprep using microwave lysis," 1994, Biotechniques 16:990–994.

Goodwin et al., "Microwave miniprep of total genomic DNA from fungi, plants protists and animals for PCR," 1993, Biotechniques, 15:438–444.

Jones et al., "An oligonucleotide probe to assay lysis and DNA hybridization of a diverse set of bacteria," 1989, Anal. Chem. 181:23–27.

Bollet et al., "A simple method for the isolation of chromosomal DNA from Gram positive or acid–fast bacteria," 1991, Nucleic Acids Res. 19:1955.

Cheyrou et al., "Improved detection of HBV DNA by PCR after microwave treatment of serum," 1991, Nucleic Acids Res. 19:4006.

Jacobsen, C.S., "Microscale detection of specific bacterial DNA in soil with a magnetic capture–hybridization and PCR amplification Assay," 1995, Appl. Environm. Microbiol. 61:3347–3352.

Vogelstein et al., "Preparative and analytical purification of DNA from agarose," 1979, Proc. Natl. Acad. Sci. 76:615.

Partlow et al., "Effects of millimeter–wave radiation on monolyer cell cultures. 1.design and validation of a novel exposure sustem," Bioelectromagnetics, 2:123–140 (1981).

Ponne et al., "Effect of radio frequency enerby on biological membranes and microorganisms," Food Science and Technology LWT, 29:41–48 (1996).

Fujikawa et al., "Patterns of bacteria destruction in solutions by microwave irradiation," J. of Applied Bacteriology, 76:389–394 (1994).

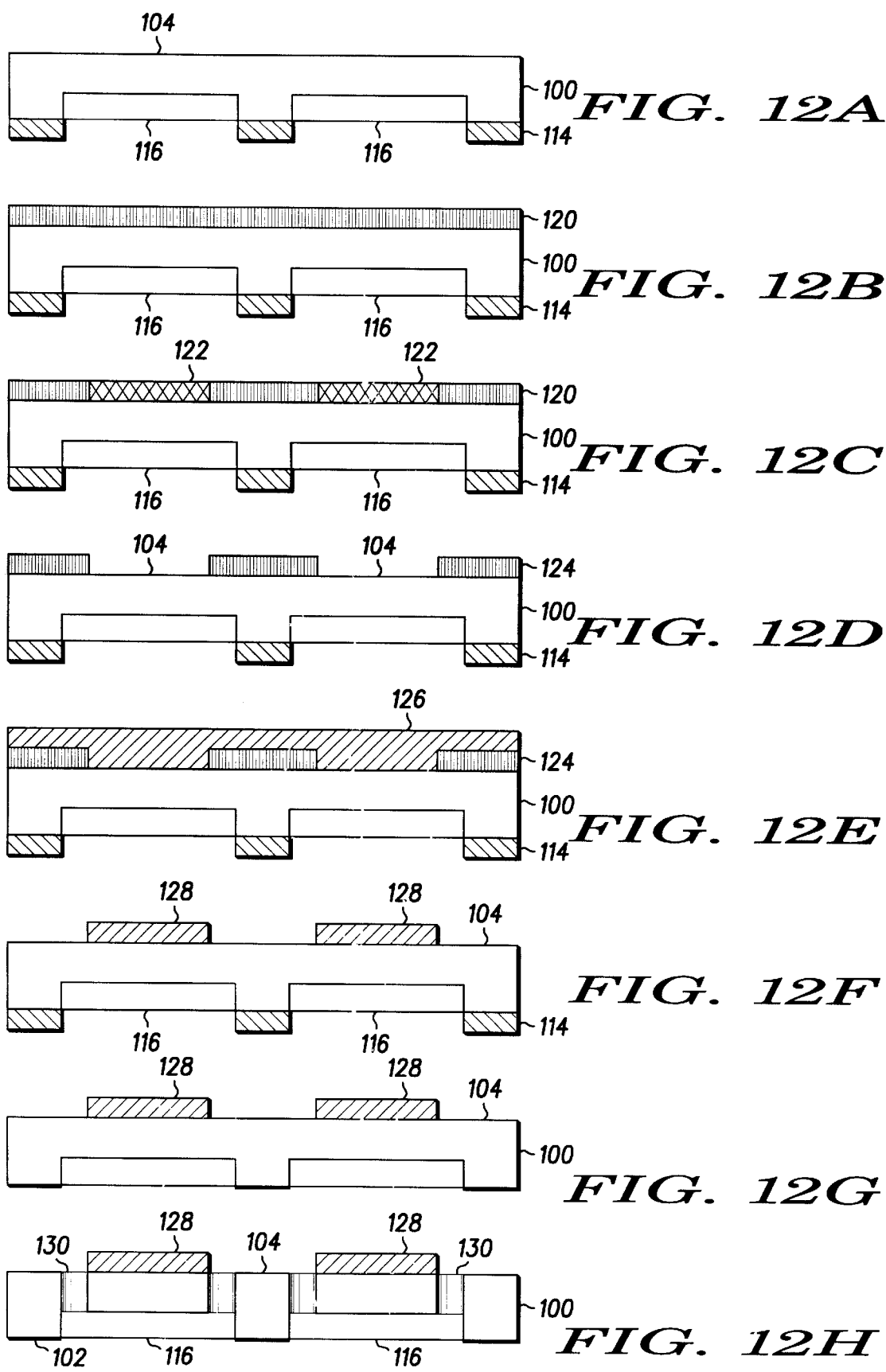

MICROFLUIDIC DEVICES WITH MONOLITHIC MICROWAVE INTEGRATED CIRCUITS

The present invention is a continuing application of U.S. Ser. No. 09/397,691, filed Sep. 16, 1999, expressly incorporated herein by reference.

The United States Government has a paid-up license in this invention and the right in limited circumstances to require the patent owner to license others on reasonable terms as provided for by the terms of National Institute of Standards and Technology, Advanced Technology Program Grant No. 70NANB9H3012.

FIELD OF THE INVENTION

The present invention is related to microfluidic devices and methods of using the same. More specifically, the present inventions provides a microfluidic device with a monolithic microwave integrated circuit and methods of using the same.

BACKGROUND OF THE INVENTION

There has been tremendous growth over the past several years in the fabrication of microfluidic devices. Monolithic microfabrication technology now permits the assembly of a multiplicity of different devices in one compact, interconnected system. For example, individual microfluidic accessories such as mixers, micro-contactors, reactors, pumps, valves, heaters, mixers and species detectors for microliter to nanoliter quantities of solids, liquids and gases may be integrated into a substrate containing microfluidic channels connecting such components to form a microfluidic device. Integrated microinstruments may be applied to biochemical, inorganic, or organic chemical reactions to perform biomedical and environmental diagnostics, and biotechnological processing and detection. Integrated microfabricated devices can be manufactured in batch quantities with high precision, yet low cost, thereby making recyclable and/or disposable single-use devices practical. Alternatively, the instrument may consist of an array of reaction instruments, which operate in parallel to simultaneously perform a number of related reactions. Operation of such instruments is easily automated, further reducing costs. Since the analysis can be performed in situ, the likelihood of contamination is very low.

Microstructure technology offers distinct advantages over macroscale technology, including the ability to perform efficient and rapid chemical analyses at a lower cost per analysis, because of decreased sample volume requirements and increased throughput. Thermocycling of these smaller volumes/masses is much more rapid, and requires much lower power input. Small volumes and high surface-area to volume ratios provide microfabricated reaction instruments with a high level of control of the parameters of a reaction. In addition, small sample volumes are advantageous because they allow a user to perform multiple analyses in parallel using a single sample on a single chip. Smaller sample volumes are also advantageous in instances where the amount of material is limiting.

Some researchers have employed microfabrication techniques in the miniaturization of processes involved in biochemistry/biomedical testing, for example nucleic acid amplification. There is a significant trend to reduce the size of these sensors, both for sensitivity and to reduce reagent costs. Thus, a number of microfluidic devices have been developed, generally comprising a solid support with microchannels, utilizing a number of different wells, pumps, reaction chambers, and the like. See for example EP 0637996 B1; EP 0637998 B1; WO96/39260; WO97/16835; WO98/13683; WO97/16561; WO97/43629; WO96/39252; WO96115576; WO96/15450; WO97/37755; and WO97/27324; and U.S. Pat. Nos. 5,304,487; 5,071531; 5,061,336; 5,747,169; 5,296,375; 5,110,745; 5,587,128; 5,498,392; 5,643,738; 5,750,015; 5,726,026; 5,35,358; 5,126,022; 5,770,029; 5,631,337; 5,569,364; 5,135,627; 5,632,876; 5,593,838; 5,585,069; 5,637,469; 5,486,335; 5,755,942; 5,681,484; and 5,603,351, all of which are expressly incorporated herein by reference.

In particular, U.S. Pat. No. 5,639,423, to Northrup et al., incorporated herein by reference in its entirety for all purposes, describe an integrated micro fabricated device for amplification of previously extracted nucleic acid by polymerase chain reaction (PCR). Northrup et al. describe lysing target cells and separating the nucleic acid from the lysate by standard macroscopic techniques. The separated nucleic acid is introduced into a reaction chamber in the microstructure and appropriate PCR reagents are added thereto via a series of micro pumps, microchannels and micro valves. Thermocycling for PCR amplification is accomplished by resistive heating elements incorporated into the microdevice and adjacent to the reaction chamber. Resistive heating has several disadvantages. The resistive element and its surrounding thermally conductive material retains energy, which will continue to heat the sample even after the power is shut down to the element. Additionally, heat transfer depends substantially on passive conduction mechanisms.

Microstructures have also been described to accomplish cell lysis with and without PCR amplification. U.S. Pat. No. 5,304,487 to Wilding et al., incorporated herein by reference in its entirety for all purposes, discusses the use of physical protrusions within microchannels or sharp edged particles within a chamber or channel to mechanically lyse the cell, after which the lysate is tested (to determine what type of cell is present for example). Waters et al. describe thermally lysing cells in a micro-reaction chamber containing the PCR amplification reagents by heating the entire device in a commercial thermocycler. Waters et al., Microchip Device for Cell Lysis, Multiplex PCR Amplification, and Electrophoretic Sizing, Anal. Chem 70:158–162 (1998) (incorporated herein by reference). The entire device is then thermocyled to amplify the nucleic acid within the lysate, after which an intercalating dye is added. The amplified nucleic acid lysate solution is then loaded from the micro-reaction chamber onto a micro-electrophoretic sizing column, which is connected by a micro valve to the lysing/PCR reaction chamber, and the nucleic acid contents within the lysate are sized.

On the macroscopic scale, nucleic acid extraction can be accomplished in a number of different ways, for example, mechanical, chemical, enzymatic, thermal or any combination thereof. Several researchers have reported that exposing cells to microwave radiation in combination with other extraction techniques enhances nucleic acid extraction from cells and virus and shortens the time required therefore. For example, Hultner and Cleaver (hereinafter Hultner et al.) exposed cells, resuspended in 400 $\mu$L of STET/lysozyme buffer solution, to microwave radiation. A Bacterial Plasmid DNA Miniprep Using Microwave Lysis, Bio Techniques 6:990–993 (1994). Hultner et al. further report that 15–20 seconds of microwave exposure was sufficient to achieve plasmid recovery compared to 40 seconds using the more conventional boiling-lysis method, and that applying microwave radiation achieved more reliable (i.e., lower failure rate) results. Id. Goodwin and Lee (hereinafter Goodwin et al.) applied microwave plasmid radiation for approximately 30 seconds to eukaryotic cells in a standard volume of lysis buffer, added additional lysis buffer, and incubated the resulting solution for 10 minutes. Goodwin et al. report that this method achieved results comparable to the standard more laborious methods, and reduced incubation times to approximately 10 minutes from approximately an hour in the other methods. Jones et al. used microwave irradiation in the filter lysis technique and demonstrated that 51 of 59 bacterial species yielded genetic material detectable by standard nucleic acid hybridization techniques. An Oligonucleotide Probe to Assay Lysis and DNA Hybridization of a Diverse Set of Bacteria, Anal. Microchem. 181:23–27 (1989) (microwave irradiation applied in filter lysis technique. Bollet et a. report enhanced lysis of Gram positive pathogens by applying microwave radiation during a standard detergent extraction procedure. A Simple Method for the Isolation of Chromosomal DNA from Gram Positive or Acid-fast Bacteria, Nucl. Acids Research 19:1955 (1991). Cheyrou et al. report exposing a 10 $\mu$L serum sample to microwave radiation for 2–4 minutes, and using the desicated preparation directly for PCR analysis of Hepatitis B Virus. Improved Detection of HBV DNA by PCR after Microwave Treatment of Serum, Nucl. Acids Research 19:4006 (1991). Cheyrou et al. propose that the microwave radiation mediated the denaturation of serum-associated PCR inhibitory factors. In all of these studies microwave radiation was applied by placing the sample in a conventional microwave oven. Additionally, microwave irradiation has proved useful for achieving enhanced or more specific results in chemical reactions of many types. See, e.g., Whittaker, G., Fast and Furious, New Scientist, Feg. 28, 1998, p. 34–37.

Given the desire to conduct chemical reactions and processes in microfluidic devices (such as nucleic acid extraction, amplification and further processing thereof), there is a need in the art to improve the performance of these devices. Microwave radiation applied to chemical reactions and processes, including nucleic acid extraction from microorganisms, has proven to enhance, or sometimes make possible the desired result. Thus, there is a need in the art for microfluidic devices in which microwave radiation can be applied to the reaction cavities within the device.

SUMMARY OF THE INVENTION

The present invention is directed to a microfluidic device having a monolithic microwave integrated circuit (MMIC) for applying microwave radiation to a cavity within the microfluidic device. The MMIC may have a microstrip design, slot design, or a coplanar design. In one embodiment the MMIC is used for lysing cells, in other emodiments the MMIC is used to heat a sample.

The present invention also provides methods for lysing cells in a microfluidic device. The cells are introduced into a cavity within the device microwave radiation is applied to the cavity from a monolithic microwave integrated circuit. The method may further comprise separating a target analyte, for example and without limitation nucleic acid, from the lysate.

DESCRIPTION OF THE DRAWINGS

FIGS. 12A–H are cross-sectional schematic views of the structures formed after various steps in the process of fabricating a microfluidic device having a monolithic microwave integrated circuit, in accordance with a preferred embodiment of the present invention;

DETAILED DESCRIPTION OF THE PREFERRED EMBODIMENTS

Figure 1:
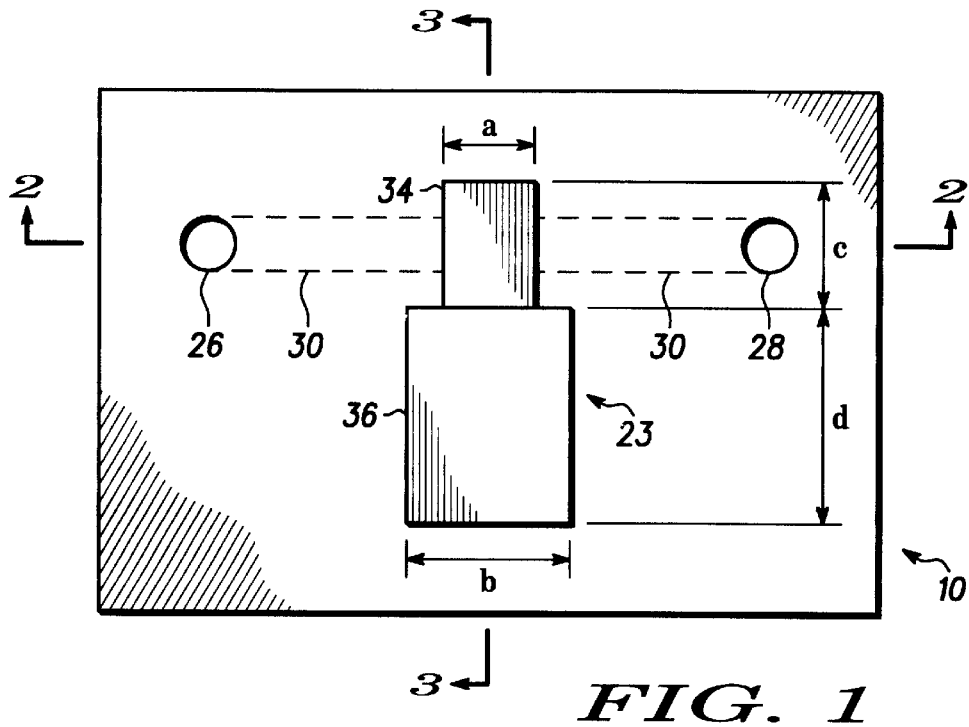
FIG. 1 is a plan view of a microfluidic with a microstrip monolithic microwave integrated circuit, in accordance with an embodiment of the present invention.

The present invention provides a device and method for applying substantially localized microwave radiation to samples in a microfluidic device. More specifically, the present invention provides microfluidic cassettes or devices (hereinafter "microfluidic device" or "device") that have a monolithic microwave integrated circuit (MMIC) integrated into the device. The MMIC is used to apply microwave radiation to a cavity defined by the device for enhancing a reaction or process taking place therein. In addition, as outlined herein, the devices of the invention can include without limitation: one or more wells for sample manipulation, waste or reagents; microchannels to and between these wells, including microchannels containing electrophoretic separation matrices; valves to control fluid movement; and on-chip pumps. The devices of the invention can be configured to manipulate one or multiple samples.

The MMIC designs of the present invention include, but are not limited to, microstrip designs, slot designs, and coplanar designs. See, e.g., *Gallium Arsenide Technology, Chs. 6–7* edited by David Kerry (Howard W. Sams & Co. 1985); *Microwave Circuit Analysis and Amplifier Design*, Liao S.(Prentice-Hall, 1987); *Computer Aided Design of Microwave Circuits*, Gupta et al. (Artech House 1981) all of which are incorporated herein in their entirety by reference.

In a preferred embodiment, the MMIC designs of the present invention provide high frequency resonance absorption and low power consumption. By integration of an appropriate microwave circuit into a microfluidic device in accordance with the present invention, a precise, reliable and substantially localized application of microwave radiation to a sample in the microfluidic device is made possible; as the skilled artisan will appreciate, this enhances or makes possible many types of reactions and processes within a microfluidic device. For example, and without limitation, microwave irradiation has been shown to improve nucleic acid extraction from microorganisms, which is an essential step in many biochemical and biomedical processes (e.g., gene detection, gene sequencing, single-nucleotide-polymorphism detection). Moreover, in copending and co-assigned U.S. Ser. No. 09/347,691 (filed Sep. 16, 1999), incorporated herein in its entirety by reference for all purposes, it has been demonstrated that the use of higher frequencies (e.g., 18–26 GHz) significantly enhances the ability to heat smaller samples characteristic of those used in microfluidic processes.

Accordingly, the present invention provides MMIC devices. As used herein, the term "monolithic microwave integrated circuit" or "MMIC" refers to a combination of interconnected microwave circuit elements integrated on a substrate.

The integrated circuits are on a substrate. The composition of the solid substrate will depend on a variety of factors, including the techniques used to create the device, the use of the device, the composition of the sample, the analyte to be detected, the size of the wells and microchannels, the presence or absence of elecronic components, etc. Generally, the devices of the invention should be easily sterilizable as well.

In a preferred embodiment, the solid substrate can be made from a wide variety of materials, including, but not limited to, silicon such as silicon wafers, silcon dioxide, silicon nitride, ceramics, glass and fused silica, gallium arsenide, indium phosphide, aluminum, ceramics, polyimide, quartz, plastics, resins and polymers including polymethylmethacrylate, acrylics, polyethylene, polyethylene terepthalate, polycarbonate, polystyrene and other styrene copolymers, polypropylene, polytetrafluoroethylene, superalloys, KOVAR, KEVLAR, KAPTON, MYLAR, sapphire, etc. High quality glasses such as high melting borosilicate or fused silicas may be preferred for their UV transmission properties when any of the sample manipulation steps require light based technologies. In addition, as outlined herein, portions of the internal surfaces of the device may be coated with a variety of coatings as needed, to reduce non-specific binding, to allow the attachment of binding ligands, for biocompatibility, for flow resistance, etc. Most preferably, the substrates are made from or glass (for accuracy and stiffness), molded plastics (which reduce cost of manufacture and thermal inertia), or ceramics (for the incorporation of microfluidic elements).

For example, in a preferred embodiment, the solid support comprises ceramic materials, such as are outlined in U.S. Ser. Nos. 09/235,081; 09/337,086; 09/464,490; 09/492,013; 09/466,325; 09/460,281; 09/460,283; 09/387,691; 09/438,600; 09/506,178; and 09/458,534; all of which are expressly incorporated by reference in their entirety. In an embodiment of the present invention, the devices are made from layers of green-sheet that have been laminated and sintered together to form a substantially monolithic structure. The green-sheet layers are laminated together and then fired to form a substantially monolithic multilayered structure. The manufacturing, processing, and applications of ceramic green-sheets are described generally in Richard E. Mistler, "Tape Casting: The Basic Process for Meeting the Needs of the Electronics Industry," Ceramic Bulletin, vol. 69, no. 6, pp. 1022–26 (1990), and in U.S. Pat. No. 3,991,029, which are incorporated herein by reference. Glass and plastic are particularly preferred for their low cost compared to silicon. Most preferably, substrate is made from glass. Alternatively, plastic may be used as the substrate material.

Included within the device are cavities (sometimes referred to herein as "wells" or "reaction chambers"). The term "cavity" as used herein means a void within or on a microfluidic device into which or through which a fluid may flow or be stored. For example and without limitation, a cavity includes channels, wells, or chambers. Chambers may also vary in size and shape. For example, in some cases, circular chambers may be employed. Alternatively, elongate chambers may be used. In general however, the chambers will be from about 0.05 to about 20 $\mu$m in width or diameter, preferably from about 0.1 or 0.5 to about 20 $\mu$m in width or diameter and about 0.05 to about 5 $\mu$m deep, and preferably 0.05 to about 1 $\mu$m deep. For elongate chambers, length will also typically vary along these same ranges.

In a preferred embodiment, the devices comprise conductors for the transition of microwave radiation. Suitable conductors include, but are not limited to, microstrip line conductors and slot line conductors, both of which are well known in the art.

The position, orientation and number of conductors can vary widely, as will be appreciated by those in the art. In a preferred embodiment, the conductors are placed adjacent to the cavity for which heating and/or lysing is desired. By "adjacent" herein is meant that the conductors are close enough to allow heating of the sample within the cavity.

In addition to the components, particularly microwave components outlined herein, the devices of the invention can include one or more wells for sample manipulation, waste or reagents; microchannels to and between these wells, including microchannels containing electrophoretic separation matrices; valves to control fluid movement; on-chip pumps such as electroosmotic, electrohydrodynamic, or electrokinetic pumps; and detection systems comprising electrodes, as is more fully described below. The devices of the invention can be configured to manipulate one or multiple samples or analytes.

In a preferred embodiment, the solid substrate is configured for handling a single sample that may contain a plurality of target analytes. That is, a single sample is added to the device and the sample may either be aliquoted for parallel processing for detection of the analytes or the sample may be processed serially, with individual targets being detected in a serial fashion. In addition, samples may be removed periodically or from different locations for in line sampling.

In a preferred embodiment, the solid substrate is configured for handling multiple samples, each of which may contain one or more target analytes. In general, in this embodiment, each sample is handled individually; that is, the manipulations and analyses are done in parallel, with preferably no contact or contamination between them. Alternatively, there may be some steps in common; for example, it may be desirable to process different samples separately but detect all of the target analytes on a single detection electrode, as described below.

In addition, it should be understood that while most of the discussion herein is directed to the use of planar substrates with microchannels and wells, other geometries can be used as well. For example, two or more planar substrates can be stacked to produce a three dimensional device, that can contain microchannels flowing within one plane or between planes; similarly, wells may span two or more substrates to allow for larger sample volumes. Thus for example, both sides of a substrate can be etched to contain microchannels; see for example U.S. Pat. Nos. 5,603,351 and 5,681,484, both of which are hereby incorporated by reference.

Thus, the devices of the invention include at least one microchannel or flow channel that allows the flow of sample from the sample inlet port to the other components or modules of the system. The collection of microchannels and wells is sometimes referred to in the art as a "mesoscale flow system". As will be appreciated by those in the art, the flow channels may be configured in a wide variety of ways, depending on the use of the channel. For example, a single flow channel starting at the sample inlet port may be separated into a variety of smaller channels, such that the original sample is divided into discrete subsamples for parallel processing or analysis. Alternatively, several flow channels from different modules, for example the sample inlet port and a reagent storage module may feed together into a mixing chamber or a reaction chamber. As will be appreciated by those in the art, there are a large number of possible configurations; what is important is that the flow channels allow the movement of sample and reagents from one part of the device to another. For example, the path lengths of the flow channels may be altered as needed; for example, when mixing and timed reactions are required, longer and sometimes tortuous flow channels can be used.

In general, the microfluidic devices of the invention are generally referred to as "mesoscale" devices. The devices herein are typically designed on a scale suitable to analyze microvolumes, although in some embodiments large samples (e.g. cc's of sample) may be reduced in the device to a small volume for subsequent analysis. That is, "mesoscale" as used herein refers to chambers and microchannels that have cross-sectional dimensions on the order of 0.1 $\mu$m to 500 $\mu$m. The mesoscale flow channels and wells have preferred depths on the order of 0.1 $\mu$m to 100 $\mu$m, typically 2–50 $\mu$m. The channels have preferred widths on the order of 2.0 to 500 pm, more preferably 3–100 $\mu$m. For many applications, channels of 5–50 $\mu$m are useful. However, for many applications, larger dimensions on the scale of millimeters may be used. Similarly, chambers (sometimes also referred to herein as "wells") in the substrates often will have larger dimensions, on the scale of a few millimeters.

In addition to the flow channel system, the devices of the invention are configured to include one or more of a variety of components, herein referred to as "modules", that will be present on any given device depending on its use. These modules include, but are not limited to: sample inlet ports; sample introduction or collection modules; cell handling modules (for example, for cell lysis (including the microwave lysis of cells as described herein), cell removal, cell concentration, cell separation or capture, cell growth, etc.); separation modules, for example, for electrophoresis, gel filtration, ion exchange/affinity chromatography (capture and release) etc.; reaction modules for chemical or biological alteration of the sample, including amplification of the target analyte (for example, when the target analyte is nucleic acid, amplification techniques are useful, including, but not limited to polymerase chain reaction (PCR), ligase chain reaction (LCR), strand displacement amplification (SDA), and nucleic acid sequence based amplification (NASBA)), chemical, physical or enzymatic cleavage or alteration of the target analyte, or chemical modification of the target; fluid pumps; fluid valves; thermal modules for heating and cooling; storage modules for assay reagents; mixing chambers; and detection modules.

In a preferred embodiment, the devices of the invention include at least one sample inlet port for the introduction of the sample to the device. This may be part of or separate from a sample introduction or collection module; that is, the sample may be directly fed in from the sample inlet port to a separation chamber, or it may be pretreated in a sample collection well or chamber.

In a preferred embodiment, the devices of the invention include a sample collection module, which can be used to concentrate or enrich the sample if required; for example, see U.S. Pat. No. 5,770,029, including the discussion of enrichment channels and enrichment means.

In a preferred embodiment, the devices of the invention include a cell handling module. This is of particular use when the sample comprises cells that either contain the target analyte or that must be removed in order to detect the target analyte. Thus, for example, the detection of particular antibodies in blood can require the removal of the blood cells for efficient analysis, or the cells (and/or nucleus) must be lysed prior to detection. In this context, "cells" include eukaryotic and prokaryotic cells as outlined herein, and viral particles that may require treatment prior to analysis, such as the release of nucleic acid from a viral particle prior to detection of target sequences. In addition, cell handling modules may also utilize a downstream means for determining the presence or absence of cells. Suitable cell handling modules include, but are not limited to, cell lysis modules, cell removal modules, cell concentration modules, and cell separation or capture modules. In addition, as for all the modules of the invention, the cell handling module is in fluid communication via a flow channel with at least one other module of the invention.

In a preferred embodiment, the cell handling module includes a cell lysis module utilizing microwaves, as outlined herein.

Alternatively, when the microwave module is used to heat samples rather than lyse cells, other forms of cell lysis can be done. For example, as is known in the art, cells may be lysed in a variety of ways, depending on the cell type. In one embodiment, as described in EP 0 637 998 B1 and U.S. Pat. No. 5,635,358, hereby incorporated by reference, the cell lysis module may comprise cell membrane piercing protrusions that extend from a surface of the cell handling module. As fluid is forced through the device, the cells are ruptured. Similarly, this may be accomplished using sharp edged particles trapped within the cell handling region. Alternatively, the cell lysis module can comprise a region of restricted cross-sectional dimension, which results in cell lysis upon pressure.

In a preferred embodiment, the cell lysis module comprises a cell lysing agent, such as guanidium chloride, chaotropic salts, enzymes such as lysozymes, etc. In some embodiments, for example for blood cells, a simple dilution with water or buffer can result in hypotonic lysis. The lysis agent may be solution form, stored within the cell lysis module or in a storage module and pumped into the lysis module. Alternatively, the lysis agent may be in solid form, that is taken up in solution upon introduction of the sample.

The cell lysis module may also include, either internally or externally, a filtering module for the removal of cellular debris as needed. This filter may be microfabricated between the cell lysis module and the subsequent module to enable the removal of the lysed cell membrane and other cellular debris components; examples of suitable filters are shown in EP 0 637 998 B1, incorporated by reference.

In a preferred embodiment, the cell handling module includes a cell separation or capture module. This embodiment utilizes a cell capture region comprising binding sites capable of reversibly binding a cell surface molecule to enable the selective isolation (or removal) of a particular type of cell from the sample population, for example, white blood cells for the analysis of chromosomal nucleic acid, or subsets of white blood cells. These binding moieties may be immobilized either on the surface of the module or on a particle trapped within the module (i.e. a bead) by physical absorption or by covalent attachment. Suitable binding moieties will depend on the cell type to be isolated or removed, and generally includes antibodies and other binding ligands, such as ligands for cell surface receptors, etc. Thus, a particular cell type may be removed from a sample prior to further handling, or the assay is designed to specifically bind the desired cell type, wash away the non-desirable cell types, followed by either release of the bound cells by the addition of reagents or solvents, physical removal (i.e. higher flow rates or pressures), or even in situ lysis.

Alternatively, a cellular "sieve" can be used to separate cells on the basis of size. This can be done in a variety of ways, including protrusions from the surface that allow size exclusion, a series of narrowing channels, a weir, or a diafiltration type setup.

In a preferred embodiment, the cell handling module includes a cell removal module. This may be used when the sample contains cells that are not required in the assay or are undesirable. Generally, cell removal will be done on the basis of size exclusion as for "sieving", above, with channels exiting the cell handling module that are too small for the cells.

In a preferred embodiment, the cell handling module includes a cell concentration module. As will be appreciated by those in the art, this is done using "sieving" methods, for example to concentrate the cells from a large volume of sample fluid prior to lysis.

In a preferred embodiment, the devices of the invention include a separation module. Separation in this context means that at least one component of the sample is separated from other components of the sample. This can comprise the separation or isolation of the target analyte, or the removal of contaminants that interfere with the analysis of the target analyte, depending on the assay.

In a preferred embodiment, the separation module includes chromatographic-type separation media such as absorptive phase materials, including, but not limited to reverse phase materials (e.g. $C_8$ or $C_{18}$ coated particles, etc.), ion-exchange materials, affinity chromatography materials such as binding ligands, etc. See U.S. Pat. No. 5,770,029, herein incorporated by reference.

In a preferred embodiment, the separation module utilizes binding ligands, as is generally outlined herein for cell separation or analyte detection. In this embodiment, binding ligands are immobilized (again, either by physical absorption or covalent attachment, described below) within the separation module (again, either on the internal surface of the module, on a particle such as a bead, filament or capillary trapped within the module, for example through the use of a frit). Suitable binding moieties will depend on the sample component to be isolated or removed. By "binding ligand" or grammatical equivalents herein is meant a compound that is used to bind a component of the sample, either a contaminant (for removal) or the target analyte (for enrichment). In some embodiments, as outlined below, the binding ligand is used to probe for the presence of the target analyte, and that will bind to the analyte.

As will be appreciated by those in the art, the composition of the binding ligand will depend on the sample component to be separated. Binding ligands for a wide variety of analytes are known or can be readily found using known techniques. For example, complementary nucleic acids can be used as the binding ligands for single stranded target nucleic acids. Similarly, when the component is a protein, the binding ligands include proteins (particularly including antibodies or fragments thereof (FAbs, etc.)) or small molecules. When the sample component is a metal ion, the binding ligand generally comprises traditional metal ion ligands or chelators. Preferred binding ligand proteins include peptides. For example, when the component is an enzyme, suitable binding ligands include substrates and inhibitors. Antigen-antibody pairs, receptor-ligands, and carbohydrates and their binding partners are also suitable component-binding ligand pairs. The binding ligand may be nucleic acid, when nucleic acid binding proteins are the targets; alternatively, as is generally described in U.S. Pat. Nos. 5,270,163, 5,475,096, 5,567,588, 5,595,877, 5,637, 459, 5,683,867, 5,705,337, and related patents, hereby incorporated by reference, nucleic acid "aptomers" can be developed for binding to virtually any target analyte. Similarly, there is a wide body of literature relating to the development of binding partners based on combinatorial chemistry methods. In this embodiment, when the binding ligand is a nucleic acid, preferred compositions and techniques are outlined in PCT US97/20014, hereby incorporated by reference.

In a preferred embodiment, the binding of the sample component to the binding ligand is specific, and the binding ligand is part of a binding pair. By "specifically bind" herein is meant that the ligand binds the component, for example the target analyte, with specificity sufficient to differentiate between the analyte and other components or contaminants of the test sample. The binding should be sufficient to remain bound under the conditions of the separation step or assay, including wash steps to remove non-specific binding. In some embodiments, for example in the detection of certain biomolecules, the disassociation constants of the analyte to the binding ligand will be less than about $10^{-4}$--$10^{-6}$ $M^{-1}$, with less than about $10^{-5}$ to $10^{-9}$ $M^{-1}$ being preferred and less than about $10^{-7}$--$10^{-9}$ $M^{-1}$ being particularly preferred.

As will be appreciated by those in the art, the composition of the binding ligand will depend on the composition of the target analyte. Binding ligands to a wide variety of analytes are known or can be readily found using known techniques. For example, when the analyte is a single-stranded nucleic acid, the binding ligand is generally a substantially complementary nucleic acid. Similarly the analyte may be a nucleic acid binding protein and the capture binding ligand is either a single-stranded or double-stranded nucleic acid; alternatively, the binding ligand may be a nucleic acid binding protein when the analyte is a single or double-stranded nucleic acid. When the analyte is a protein, the binding ligands include proteins or small molecules. Preferred binding ligand proteins include peptides. For example, when the analyte is an enzyme, suitable binding ligands include substrates, inhibitors, and other proteins that bind the enzyme, i.e. components of a multi-enzyme (or protein) complex. As will be appreciated by those in the art, any two molecules that will associate, preferably specifically, may be used, either as the analyte or the binding ligand. Suitable analyte/binding ligand pairs include, but are not limited to, antibodies/antigens, receptors/ligand, proteins/nucleic acids; nucleic acids/nucleic acids, enzymes/substrates and/or inhibitors, carbohydrates (including glycoproteins and glycolipids)/lectins, carbohydrates and other binding partners, proteins/proteins; and protein/small molecules. These may be wild-type or derivative sequences.

When the sample component bound by the binding ligand is the target analyte, it may be released for detection purposes if necessary, using any number of known techniques, depending on the strength of the binding interaction, including changes in pH, salt concentration, temperature, etc. or the addition of competing ligands, detergents, chaotropic agents, organic compounds, or solvents, etc.

In some embodiments, preferential binding of molecules to surfaces can be achieved using coating agents or buffer conditions; for example, DNA and RNA may be differentially bound to glass and other surfaces depending on the conditions, such as generally described below for magnetic beads.

In a preferred embodiment, the separation module includes an electrophoresis module, as is generally described in U.S. Pat. Nos. 5,770,029; 5,126,022; 5,631,337; 5,569,364; 5,750,015, and 5,135,627, all of which are hereby incorporated by reference. In electrophoresis, molecules are primarily separated by different electrophoretic mobilities caused by their different molecular size, shape and/or charge. Microcapillary tubes have recently been used for use in microcapillary gel electrophoresis (high performance capillary electrophoresis (HPCE)). One advantage of HPCE is that the heat resulting from the applied electric field is efficiently disappated due to the high surface area, thus allowing fast separation. The electrophoresis module serves to separate sample components by the application of an electric field, with the movement of the sample components being due either to their charge or, depending on the surface chemistry of the microchannel, bulk fluid flow as a result of electroosmotic flow (EOF).

As will be appreciated by those in the art, the electrophoresis module can take on a variety of forms, and generally comprises an electrophoretic microchannel and associated electrodes to apply an electric field to the electrophoretic microchannel. Waste fluid outlets and fluid reservoirs are present as required.

The electrodes comprise pairs of electrodes, either a single pair, or, as described in U.S. Pat. Nos. 5,126,022 and 5,750,015, a plurality of pairs. Single pairs have generally have one electrode at each end of the electrophoretic pathway. Multiple electrode pairs may be used to precisely control the movement of sample components, such that the sample components may be continuously subjected to a plurality of electric fields either simultaneously or sequentially.

In a preferred embodiment, electrophoretic gel media may also be used. By varying the pore size of the media, employing two or more gel media of different porosity, and/or providing a pore size gradient, separation of sample components can be maximized. Gel media for separation based on size are known, and include, but are not limited to, polyacrylamide and agarose. One preferred electrophoretic separation matrix is described in U.S. Pat. No. 5,135,627, hereby incorporated by reference, that describes the use of "mosaic matrix", formed by polymerizing a dispersion of microdomains ("dispersoids") and a polymeric matrix. This allows enhanced separation of target analytes, particularly nucleic acids. Similarly, U.S. Pat. No. 5,569,364, hereby incorporated by reference, describes separation media for electrophoresis comprising submicron to above-micron sized cross-linked gel particles that find use in microfluidic systems. U.S. Pat. No. 5,631,337, hereby incorporated by reference, describes the use of thermoreversible hydrogels comprising polyacrylamide backbones with N-substituents that serve to provide hydrogen bonding groups for improved electrophoretic separation. See also U.S. Pat. Nos. 5,061,336 and 5,071,531, directed to methods of casting gels in capillary tubes.

In a preferred embodiment, the devices of the invention include a reaction module. This can include either physical, chemical or biological alteration of one or more sample components. Alternatively, it may include a reaction module wherein the target analyte alters a second moiety that can then be detected; for example, if the target analyte is an enzyme, the reaction chamber may comprise an enzyme substrate that upon modification by the target analyte, can then be detected. In this embodiment, the reaction module may contain the necessary reagents, or they may be stored in a storage module and pumped as outlined herein to the reaction module as needed.

In a preferred embodiment, the reaction module includes a chamber for the chemical modification of all or part of the sample. For example, chemical cleavage of sample components (CNBr cleavage of proteins, etc.) or chemical cross-linking can be done. PCT US97/07880, hereby incorporated by reference, lists a large number of possible chemical reactions that can be done in the devices of the invention, including amide formation, acylation, alkylation, reductive amination, Mitsunobu, Diels Alder and Mannich reactions, Suzuki and Stille coupling, chemical labeling, etc. Similarly, U.S. Pat. Nos. 5,616,464 and 5,767,259 describe a variation of LCR that utilizes a "chemical ligation" of sorts. In this embodiment, similar to LCR, a pair of primers are utilized, wherein the first primer is substantially complementary to a first domain of the target and the second primer is substantially complementary to an adjacent second domain of the target (although, as for LCR, if a "gap" exists, a polymerase and dNTPs may be added to "fill in" the gap). Each primer has a portion that acts as a "side chain" that does not bind the target sequence and acts as one half of a stem structure that interacts non-covalently through hydrogen bonding, salt bridges, van der Waal's forces, etc. Preferred embodiments utilize substantially complementary nucleic acids as the side chains. Thus, upon hybridization of the primers to the target sequence, the side chains of the primers are brought into spatial proximity, and, if the side chains comprise nucleic acids as well, can also form side chain hybridization complexes. At least one of the side chains of the primers comprises an activatable cross-linking agent, generally covalently attached to the side chain, that upon activation, results in a chemical cross-link or chemical ligation. The activatible group may comprise any moiety that will allow cross-linking of the side chains, and include groups activated chemically, photonically and thermally, with photo-activatable groups being preferred. In some embodiments a single activatable group on one of the side chains is enough to result in cross-linking via interaction to a functional group on the other side chain; in alternate embodiments, activatable groups are required on each side chain. In addition, the reaction chamber may contain chemical moieties for the protection or deprotection of certain functional groups, such as thiols or amines.

In a preferred embodiment, the reaction module includes a chamber for the biological alteration of all or part of the sample. For example, enzymatic processes including nucleic acid amplification, hydrolysis of sample components or the hydrolysis of substrates by a target enzyme, the addition or removal of detectable labels, the addition or removal of phosphate groups, etc.

In a preferred embodiment, the target analyte is a nucleic acid and the biological reaction chamber allows amplification of the target nucleic acid. Suitable amplification techniques include, both target amplification and probe amplification, including, but not limited to, polymerase chain reaction (PCR), ligase chain reaction (LCR), strand displacement amplification (SDA), self-sustained sequence replication (3SR), QB replicase amplification (QBR), repair chain reaction (RCR), cycling probe technology or reaction (CPT or CPR), nucleic acid sequence based amplification (NASBA) and rolling circle amplification (RCA). Techniques utilizing these methods and the detection modules of the invention are described in PCT US99/01705, herein incorporated by reference in its entirety. In this embodiment, the reaction reagents generally comprise at least one enzyme (generally polymerase), primers, and nucleoside triphosphates as needed.

General techniques for nucleic acid amplification are well known in the art. In most cases, double stranded target nucleic acids are denatured to render them single stranded so as to permit hybridization of the primers and other probes of the invention. A preferred embodiment utilizes a thermal step, generally by raising the temperature of the reaction to about 95° C., although pH changes and other techniques such as the use of extra probes or nucleic acid binding proteins may also be used.

In a preferred embodiment, the devices of the invention include a detection module used to detect target analytes in samples. By "target analyte" or "analyte" or grammatical equivalents herein is meant any molecule, compound or particle to be detected. As outlined below, target analytes preferably bind to binding ligands, as is more fully described above. As will be appreciated by those in the art, a large number of analytes may be detected using the present methods; basically, any target analyte for which a binding ligand, described herein, may be made may be detected using the methods of the invention.

Suitable analytes include organic and inorganic molecules, including biomolecules. In a preferred embodiment, the analyte may be an environmental pollutant (including pesticides, insecticides, toxins, etc.); a chemical (including solvents, polymers, organic materials, etc.); therapeutic molecules (including therapeutic and abused drugs, antibiotics, etc.); biomolecules (including hormones, cytokines, proteins, lipids, carbohydrates, cellular membrane antigens and receptors (neural, hormonal, nutrient, and cell surface receptors) or their ligands, etc); whole cells (including procaryotic (such as pathogenic bacteria) and eukaryotic cells, including mammalian tumor cells); viruses (including retroviruses, herpesviruses, adenoviruses, lentiviruses, etc.); and spores; etc. Particularly preferred analytes are environmental pollutants; nucleic acids; proteins (including enzymes, antibodies, antigens, growth factors, cytokines, etc); therapeutic and abused drugs; cells; and viruses.

In a preferred embodiment, the target analyte is a nucleic acid. By "nucleic acid" or "oligonucleotide" or grammatical equivalents herein means at least two nucleotides covalently linked together. A nucleic acid of the present invention will generally contain phosphodiester bonds, although in some cases, as outlined below, for example when capture probes on a surface are used in the detection module, nucleic acid analogs are included that may have alternate backbones, comprising, for example, phosphoramide (Beaucage et al., Tetrahedron 49(10):1925 (1993) and references therein; Letsinger, J. Org. Chem. 35:3800 (1970); Sprinzl et al., Eur. J. Biochem. 81:579 (1977); Letsinger et al., Nucl. Acids Res. 14:3487 (1986); Sawai et al, Chem. Lett. 805 (1984), Letsinger et al., J. Am. Chem. Soc. 110:4470 (1988); and Pauwels et al., Chemica Scripta 26:141 91986)), phosphorothioate (Mag et al., Nucleic Acids Res. 19:1437 (1991); and U.S. Pat. No. 5,644,048), phosphorodithioate (Briu et al., J. Am. Chem. Soc. 111:2321 (1989), O-methylphophoroamidite linkages (see Eckstein, Oligonucleotides and Analogues: A Practical Approach, Oxford University Press), and peptide nucleic acid backbones and linkages (see Egholm, J. Am. Chem. Soc. 114:1895 (1992); Meier et al., Chem. Int. Ed. Engl. 31:1008 (1992); Nielsen, Nature, 365:566 (1993); Carlsson et al., Nature 380:207 (1996), all of which are incorporated by reference). Other analog nucleic acids include those with positive backbones (Denpcy et al., Proc. Natl. Acad. Sci. USA 92:6097 (1995); non-ionic backbones (U.S. Pat. Nos. 5,386,023, 5,637,684, 5,602,240, 5,216,141 and 4,469,863; Kiedrowshi et al., Angew. Chem. Intl. Ed. English 30:423 (1991); Letsinger et al., J. Am. Chem. Soc. 110:4470 (1988); Letsinger et al., Nucleoside & Nucleotide 13:1597 (1994); Chapters 2 and 3, ASC Symposium Series 580, "Carbohydrate Modifications in Antisense Research", Ed. Y. S. Sanghui and P. Dan Cook; Mesmaeker et al., Bioorganic & Medicinal Chem. Lett. 4:395 (1994); Jeffs et al., J.

Biomolecular NMR 34:17 (1994); Tetrahedron Lett. 37:743 (1996)) and non-ribose backbones, including those described in U.S. Pat. Nos. 5,235,033 and 5,034,506, and Chapters 6 and 7, ASC Symposium Series 580, "Carbohydrate Modifications in Antisense Research", Ed. Y. S. Sanghui and P. Dan Cook. Nucleic acids containing one or more carbocyclic sugars are also included within the definition of nucleic acids (see Jenkins et al., Chem. Soc. Rev. (1995) pp169–176). Several nucleic acid analogs are described in Rawls, C & E News Jun. 2, 1997 page 35. All of these references are hereby expressly incorporated by reference. These modifications of the ribose-phosphate backbone may be done to facilitate the addition of electron transfer moieties, or to increase the stability and half-life of such molecules in physiological environments.

As will be appreciated by those in the art, all of these nucleic acid analogs may find use in the present invention. In addition, mixtures of naturally occurring nucleic acids and analogs can be made; for example, at the site of conductive oligomer or electron transfer moiety attachment, an analog structure may be used. Alternatively, mixtures of different nucleic acid analogs, and mixtures of naturally occuring nucleic acids and analogs may be made.

The nucleic acids may be single stranded or double stranded, as specified, or contain portions of both double stranded or single stranded sequence. The nucleic acid may be DNA, both genomic and cDNA, RNA or a hybrid, where the nucleic acid contains any combination of deoxyribo- and ribo-nucleotides, and any combination of bases, including uracil, adenine, thymine, cytosine, guanine, inosine, xathanine hypoxathanine, isocytosine, isoguanine, etc. As used herein, the term "nucleoside" includes nucleotides and nucleoside and nucleotide analogs, and modified nucleosides such as amino modified nucleosides. In addition, "nucleoside" includes non-naturally occuring analog structures. Thus for example the individual units of a peptide nucleic acid, each containing a base, are referred to herein as nucleosides.

In a preferred embodiment, the present invention provides methods of detecting target nucleic acids. By "target nucleic acid" or "target sequence" or grammatical equivalents herein means a nucleic acid sequence on a single strand of nucleic acid. The target sequence may be a portion of a gene, a regulatory sequence, genomic DNA, cDNA, RNA including mRNA and rRNA, or others. It may be any length, with the understanding that longer sequences are more specific. In some embodiments, it may be desirable to fragment or cleave the sample nucleic acid into fragments of 100 to 10,000 basepairs, with fragments of roughly 500 basepairs being preferred in some embodiments. As will be appreciated by those in the art, the complementary target sequence may take many forms. For example, it may be contained within a larger nucleic acid sequence, i.e. all or part of a gene or mRNA, a restriction fragment of a plasmid or genomic DNA, among others.

As is outlined more fully below, probes (including primers) are made to hybridize to target sequences to determine the presence or absence of the target sequence in a sample. Generally speaking, this term will be understood by those skilled in the art.

The target sequence may also be comprised of different target domains; for example, in "sandwich" type assays, a first target domain of the sample target sequence may hybridize to a capture probe and a second target domain may hybridize to a portion of an amplifier probe, a label probe, etc. In addition, the target domains may be adjacent (i.e. contiguous) or separated. For example, when ligation chain reaction (LCR) techniques are used, a first primer may hybridize to a first target domain and a second primer may hybridize to a second target domain; either the domains are adjacent, or they may be separated by one or more nucleotides, coupled with the use of a polymerase and dNTPs, as is known in the art.

The terms "first" and "second" are not meant to confer an orientation of the sequences with respect to the 5'-3' orientation of the target sequence. For example, assuming a 5'-3' orientation of the complementary target sequence, the first target domain may be located either 5' to the second domain, or 3' to the second domain.

In a preferred embodiment, the target analyte is a protein. As will be appreciated by those in the art, there are a large number of possible proteinaceous target analytes that may be detected using the present invention. By "proteins" or grammatical equivalents herein is meant proteins, oligopeptides and peptides, derivatives and analogs, including proteins containing non-naturally occurring amino acids and amino acid analogs, and peptidomimetic structures. The side chains may be in either the (R) or the (S) configuration. In a preferred embodiment, the amino acids are in the (S) or L-configuration. As discussed below, when the protein is used as a binding ligand, it may be desirable to utilize protein analogs to retard degradation by sample contaminants.

Suitable protein target analytes include, but are not limited to, (1) immunoglobulins, particularly IgEs, IgGs and IgMs, and particularly therapeutically or diagnostically relevant antibodies, including but not limited to, for example, antibodies to human albumin, apolipoproteins (including apolipoprotein E), human chorionic gonadotropin, cortisol, α-fetoprotein, thyroxin, thyroid stimulating hormone (TSH), antithrombin, antibodies to pharmaceuticals (including antieptileptic drugs (phenytoin, primidone, carbariezepin, ethosuximide, valproic acid, and phenobarbitol), cardioactive drugs (digoxin, lidocaine, procainamide, and disopyramide), bronchodilators (theophylline), antibiotics (chloramphenicol, sulfonamides), antidepressants, immunosuppresants, abused drugs (amphetamine, methamphetamine, cannabinoids, cocaine and opiates) and antibodies to any number of viruses (including orthomyxoviruses, (e.g. influenza virus), paramyxoviruses (e.g respiratory syncytial virus, mumps virus, measles virus), adenoviruses, rhinoviruses, coronaviruses, reoviruses, togaviruses (e.g. rubella virus), parvoviruses, poxviruses (e.g. variola virus, vaccinia virus), enteroviruses (e.g. poliovirus, coxsackievirus), hepatitis viruses (including A, B and C), herpesviruses (e.g. Herpes simplex virus, varicella-zoster virus, cytomegalovirus, Epstein-Barr virus), rotaviruses, Norwalk viruses, hantavirus, arenavirus, rhabdovirus (e.g. rabies virus), retroviruses (including HIV, HTLV-I and -II), papovaviruses (e.g. papillomavirus), polyomaviruses, and picornaviruses, and the like), and bacteria (including a wide variety of pathogenic and non-pathogenic prokaryotes of interest including Bacillus; Vibrio, e.g. *V. cholerae*; Escherichia, e.g. Enterotoxigenic *E. coli*, Shigella, e.g. *S. dysenteriae*; Salmonella, e.g. *S. typhi*; Mycobacterium e.g. *M. tuberculosis, M. leprae*; Clostridium, e.g. *C. botulinum, C. tetani, C. difficile, C. perfringens*; Cornyebacterium, e.g. *C. diphtheriae*; Streptococcus, *S. pyogenes, S. pneumoniae*; Staphylococcus, e.g. *S. aureus*; Haemophilus, e.g. *H. influenzae*; Neisseria, e.g. *N. meningitidis, N. gonorrhoeae*; Yersinia, e.g. *G. lamblia Y. pestis*, Pseudomonas, e.g. *P. aeruginosa, P. putida*; Chlamydia, e.g. *C. trachomatis*; Bordetella, e.g. *B. pertussis*; Treponema, e.g. *T. palladium*; and the like); (2) enzymes (and other proteins), including but not limited to, enzymes used as indicators of or treatment for heart disease, including creatine kinase, lactate dehydrogenase, aspartate amino transferase, troponin T, myoglobin, fibrinogen, cholesterol, triglycerides, thrombin, tissue plasminogen activator (tPA); pancreatic disease indicators including amylase, lipase, chymotrypsin and trypsin; liver function enzymes and proteins including cholinesterase, bilirubin, and alkaline phosphotase; aldolase, prostatic acid phosphatase, terminal deoxynucleotidyl transferase, and bacterial and viral enzymes such as HIV protease; (3) hormones and cytokines (many of which serve as ligands for cellular receptors) such as erythropoietin (EPO), thrombopoietin (TPO), the interleukins (including IL-1 through IL-17), insulin, insulin-like growth factors (including IGF-1 and -2), epidermal growth factor (EGF), transforming growth factors (including TGF-α and TGF-β), human growth hormone, transferrin, epidermal growth factor (EGF), low density lipoprotein, high density lipoprotein, leptin, VEGF, PDGF, ciliary neurotrophic factor, prolactin, adrenocorticotropic hormone (ACTH), calcitonin, human chorionic gonadotropin, cotrisol, estradiol, follicle stimulating hormone (FSH), thyroid-stimulating hormone (TSH), leutinzing hormone (LH), progeterone and testosterone; and (4) other proteins (including α-fetoprotein, carcinoembryonic antigen CEA, cancer markers, etc.).

In addition, any of the biomolecules for which antibodies may be detected may be detected directly as well; that is, detection of virus or bacterial cells, therapeutic and abused drugs, etc., may be done directly.

Suitable target analytes include carbohydrates, including but not limited to, markers for breast cancer (CA15-3, CA 549, CA 27.29), mucin-like carcinoma associated antigen (MCA), ovarian cancer (CA125), pancreatic cancer (DE-PAN-2), prostate cancer (PSA), CEA, and colorectal and pancreatic cancer (CA 19, CA 50, CA242).

These target analytes may be present in any number of different sample types, including, but not limited to, bodily fluids including blood, lymph, saliva, vaginal and anal secretions, urine, feces, perspiration and tears, and solid tissues, including liver, spleen, bone marrow, lung, muscle, brain, etc.

The detection module used to detect these target analytes may comprise a wide variety of different systems, including traditional nucleic acid biochips, including those made using photolithography techniques (Affymetrix GeneChip™), spotting techniques (Synteni and others), printing techniques (Hewlett Packard and Rosetta), bead arrays (Illumina), three dimensional "gel pad" arrays, electrode arrays, etc. A preferred embodiment utilizes detection modules comprising biochips such as outlined in WO 98/20162; WO 98/12430; WO 98/57158; WO 99/57317; PCT US00/34145; PCT US00/33499; PCT US00/33497; US 01/03412; and U.S. Ser. No. 09/492,013, all of which are expressly incorporated by reference.

Figure 2:
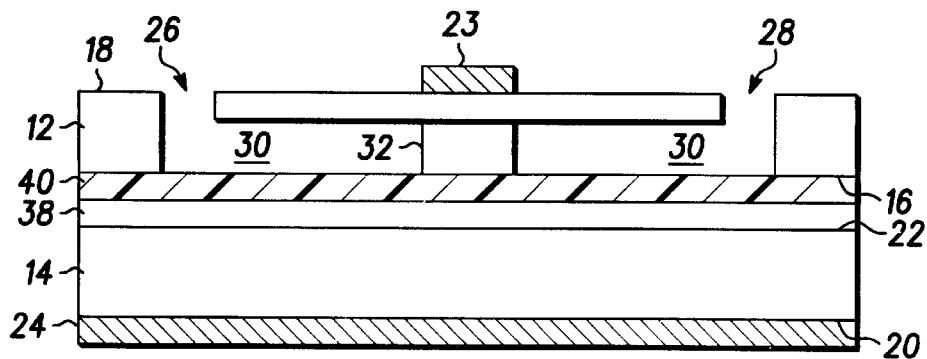
FIG. 2 is a cross-sectional view of the microfluidic device of FIG. 1, taken along line 2—2.
Figure 3:
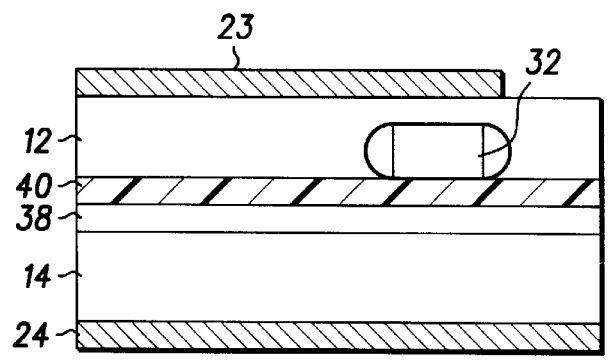
FIG. 3 is a cross-sectional view of the microfluidic device of FIG. 1, taken along line 3—3.

Referring to FIGS. 1–3, microfluidic device 10, in accordance with an embodiment of the present invention, includes top substrate 12, bottom substrate 14 and a microstrip MMIC, which is discussed in more detail below. More particularly, top substrate 12 has first surface 16 and second surface 18, and bottom substrate 14 has first surface 20 and second surface 22. The MMIC is defined by strip conductor 23 and plane conductor 24, together with the material between conductors 23 and 24. Strip conductor 23 is formed on second surface 18 of top substrate 12 and plane conductor 24 is formed on first surface 20 of bottom substrate 14. Second surface 22 of bottom substrate 14 is covered by an amorphous silicon layer 38 and an insulating layer 40.

Amorphous silicon layer 38 is provided to anodically bond top substrate 12 to bottom substrate 14. It will be appreciated by the skilled artisan that other materials and methods may be used to bond these two pieces together, such as and without limitation fusion, thermal, adhesive, pressure, or any combination thereof.

Insulating layer 40 is provided to prevent the sample from contacting the substrate in the event that the substrate material adversely effects the desired process or reaction. For example, a substrate or insulating material to which a target analyte, such as a nucleic acid, substantially irreversibly binds or absorbs would not be preferred or desirable in a device for extraction and/or purification of target analytes. Insulating layer 40 is preferably composed of a material that has good conformal properties. A preferred material for insulating layer 40 is biocompatible to prevent interaction of the material with biological samples. In a preferred embodiment, insulating layer 40 is tetraethylorthosilicate (TEOS). Insulating layer 40 preferably has a thickness of from about 100 to about 3000 Å, more preferably from about 500 to about 2000 Å and most preferably from about 1000 to about 2000 Å. It will be appreciated by the skilled artisan that the material of insulating layer 40 may be chosen to enhance the desired result, e.g., wherein the material is a reactant or catalyst in a reaction, or that insulating layer 28 may be completely absent when it is desirable or benign to have the sample contact the substrate material.

The microfluidic device 10 defines inlet port 26, outlet port 28, channels 30, and chamber 32. Chamber 32 is able to receive a small volume of a sample, typically in the range of less than a picoliter to several milliliters, preferably between about 1 nL to about 100 $\mu$L, and most preferably between about 10 nL to about 50 $\mu$L. In some circumstances, such as the direct testing of biological samples like blood, it is preferred to use between about 50 $\mu$L to about 100 $\mu$L. As the skilled artisan will appreciate, other chambers, channels or wells, in addition to chamber 32, may be integrated into device 10 without deviating from the scope of the present invention as outlined herein. For example and without limitation, cavities may be provided to hold a sample for processing or analyzing thereof. Passageways or channels may be provided for transporting a fluid within or through the device. Additionally, parallel or in-series process steps may be integrated into the microfluidic device of the present invention without exceeding the scope thereof.

As used herein, the term "channel" refers to a space with a length substantially greater than its width, or other cross-sectional dimension. Typical channels have dimensions ranging from about 10 to about 1000 $\mu$m wide, preferably 100 to 500 $\mu$m wide and about 1 to 500 $\mu$m deep. In the microfluidic devices of the present invention, channels are typically used as passageways tor transporting a sample. The sample flows along the length of the channel, typically in a horizontal orientation.

The dimensions of strip conductor 23 are designed to achieve a preselected impedance; impedance is also a function of the frequency of operation, and the properties of the substrate (i.e., dielectric properties, conductivity, etc.). An impedance of 50 ohms is preferred, which is an industry standard. The dimensions needed to obtain a desired impedance may be calculated by methods that are well-known in the art. See, e.g., *Microwave Circuit Analysis and Amplifier Design*, Liao S. (Prentice-Hall, 1987); *Computer Aided Design of Microwave Circuits,* Gupta et al. (Artech House 1981) incorporated herein in their entirety by reference. Additionally, commercial software is available for preforming the necessary design calculations, such as and without limitation HP Advanced Design Systems™ from Agilent Technologies. Thus, as will be appreciated by the skilled artisan the dimensions, and shape of strip conductor 23 may vary depending on several factors, such as and without limitation substrate material properties, shape/dimensions of the cavity to be irradiated, and the frequency of operation. In addition other design aspects should be considered, such as making a contact to the conductors, injecting a sample, etc.

In one embodiment, strip conductor 23 has a rectangular shape with a width preferably from about 1 to about 500 $\mu$m, more preferably from about 100 to about 500 $\mu$m, and most preferably about 500 $\mu$m. The length of strip conductor 23 is preferably from about 1,000 to about 20,000 $\mu$m, more preferably from about 1,000 to about 10,000 $\mu$m, and most preferably about 7,500 $\mu$m. The thickness of strip conductor 23 and ground plane conductor 24 are preferably from about 0.1 to about 1 $\mu$m, more preferably from about 0.1 to about 0.5 $\mu$m, and most preferably about 0.29 $\mu$m. Strip conductor 23 and ground plane conductor 24 may be composed of titanium (Ti), platinum (Pt), gold (Au) or a combination thereof. Preferably, strip conductor 23 and ground plane conductor 24 comprise sequential layers of Ti, Pt, Au, and Ti. Most preferably, strip conductor 23 and ground plane conductor 24 each comprise a 200 Å layer of Ti, a 500 Å layer of Pt, a 2000 Å layer of Au, and a 200 Å layer of Ti.

Strip line conductor 23, in a preferred embodiment, has first portion 34 and second portion 36. First portion 34 has width a and length c chosen to approximately match the plan view dimensions of chamber 32, into which microwave radiation will be directed. Second portion 36 has width b and length d chosen to obtain the desired impedance, as described above. The skilled artisan will appreciate that strip conductor 23 may have many different configurations without deviating from the intended scope of the present invention, and that the primary design consideration is to deliver microwave radiation to the desired location within the microfluidic device.

Substrates 12 and 14 are fabricated from any dielectric solid supporting substance as outlined herein.

Figure 4A:
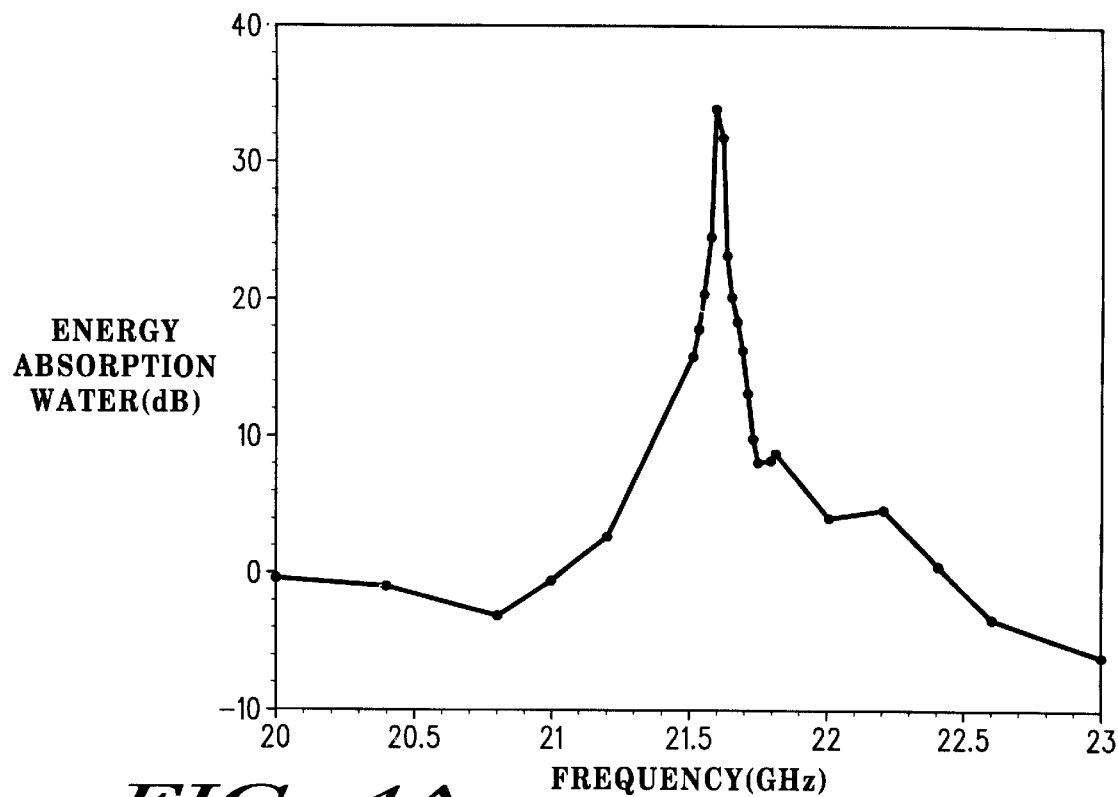
FIGS. 4A–4C are a plots of the measured energy absorption versus frequency for a sample of deionized water placed in a chamber of three microfluidic devices constructed in accordance with an embodiment of the present invention.
Figure 4B:
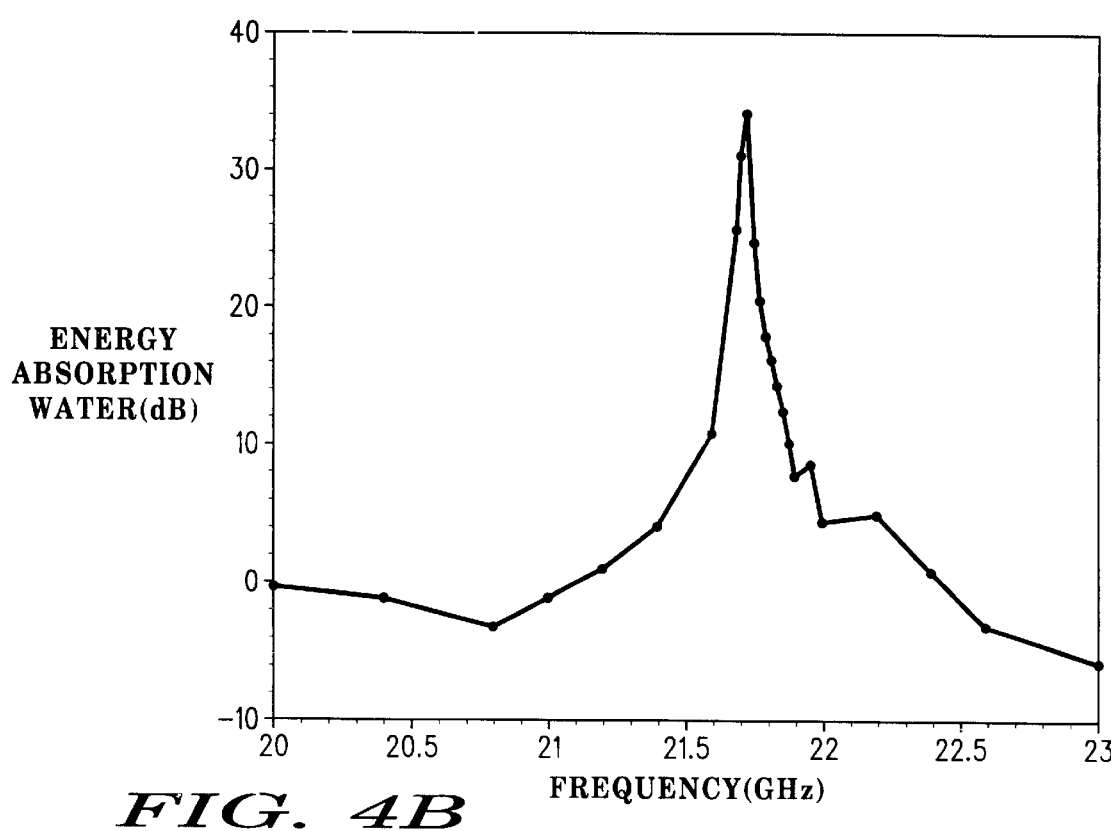
Figure 4C:
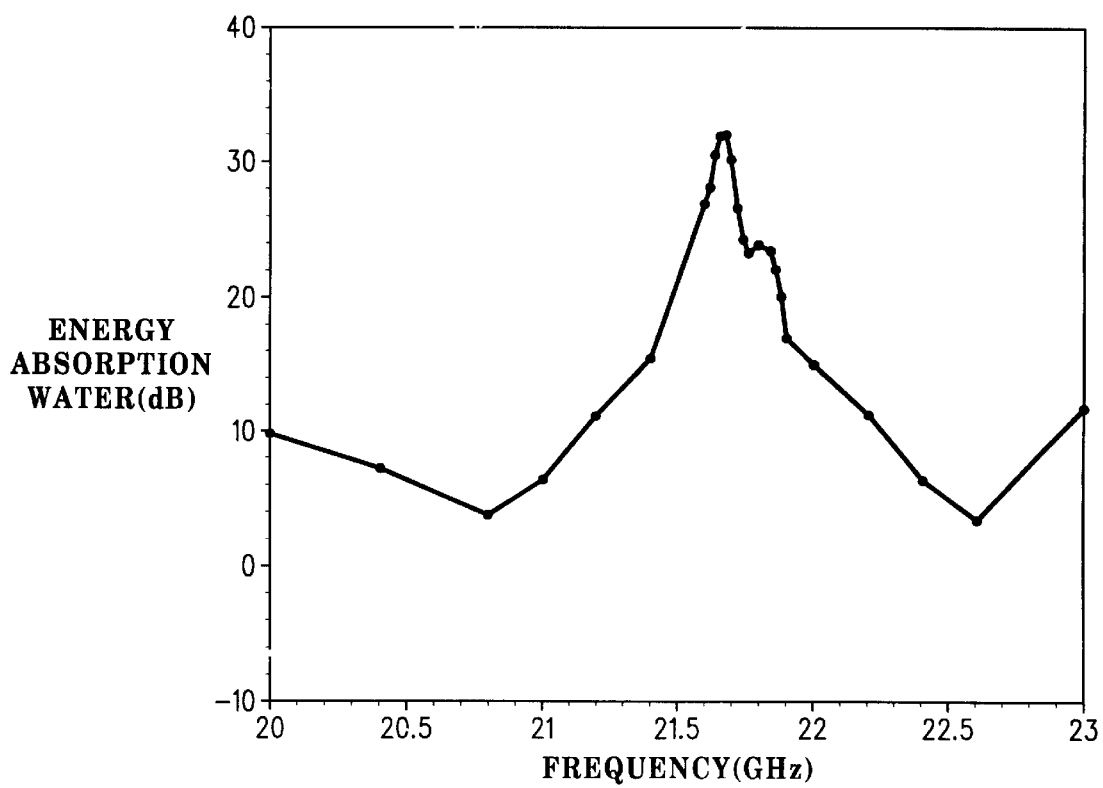

Table 1 provides the volume of chamber 32 and dimensions a, b, c, and d for three microfluidic devices with a microstrip MMIC that were fabricated in accordance with the present invention. FIGS. 4A–C show absorption of microwave energy in water versus frequency using these three designs.

TABLE 1

Metal Patterns Dimensions For Microstrip Design.

| Design | Chamber Volume ($\mu$L) | a ($\mu$m) | b ($\mu$m) | c ($\mu$m) | d ($\mu$m) |
|---|---|---|---|---|---|
| A | 25.2 | 325 | 877 | 825 | 1910 |
| B | 25.2 | 325 | 566 | 825 | 1820 |
| C | 23.26 | 500 | 500 | 552 | 6035 |

Figure 5:
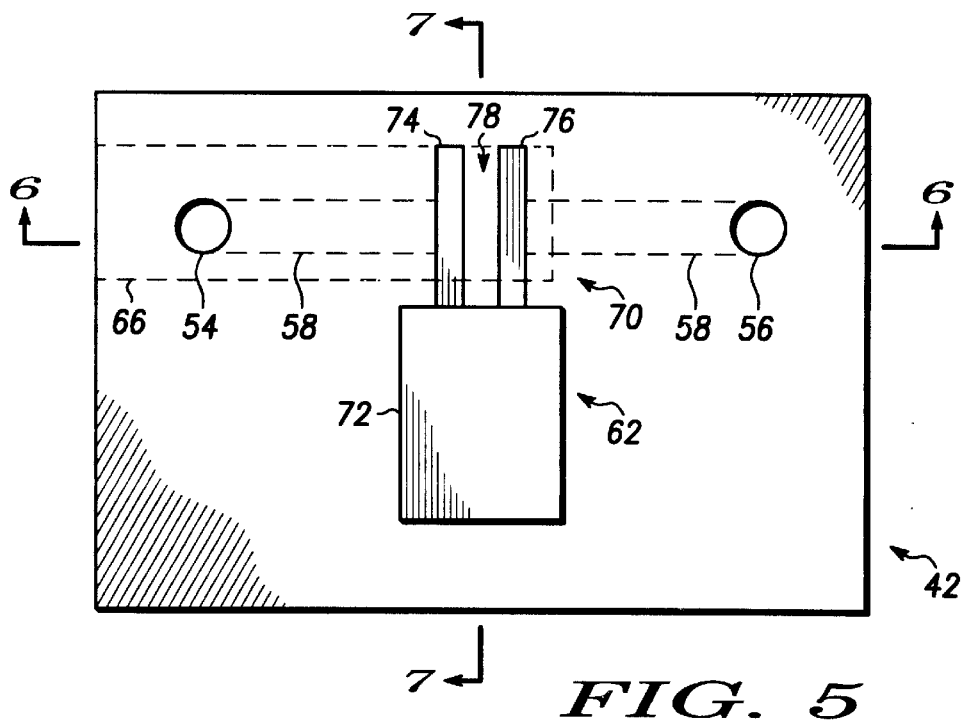
FIG. 5 is a plan view of a microfluidic device having a slot monolithic microwave integrated circuit, in accordance with an embodiment of the present invention.
Figure 6:
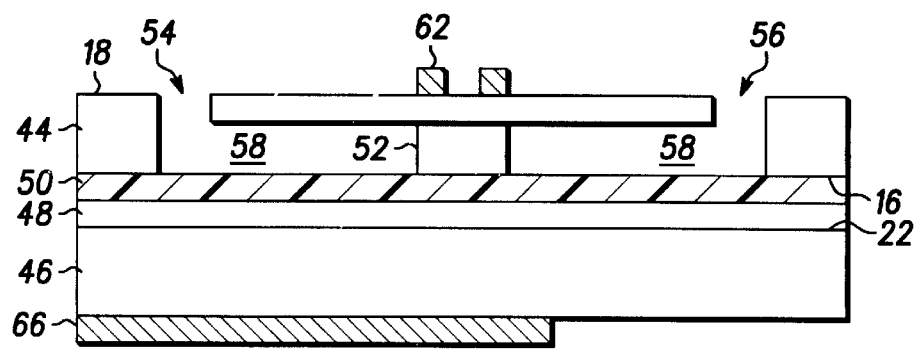
FIG. 6 is a cross-sectional view of the microfluidic device of FIG. 5, taken along line 6—6.
Figure 7:
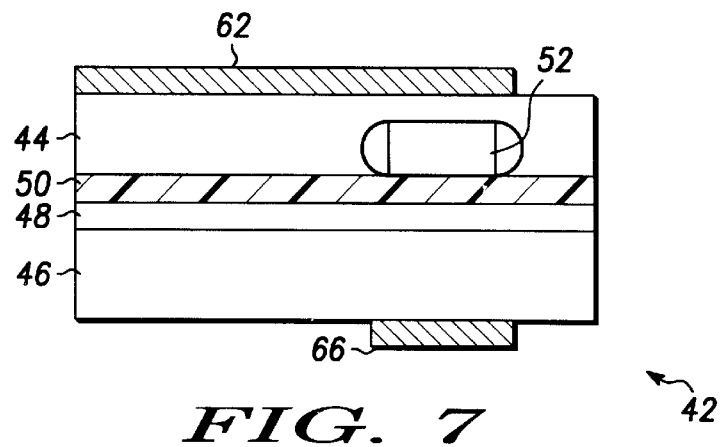
FIG. 7 is a cross-sectional view of the microfluidic device of FIG. 5, taken along line 7—7.
Figure 8B:
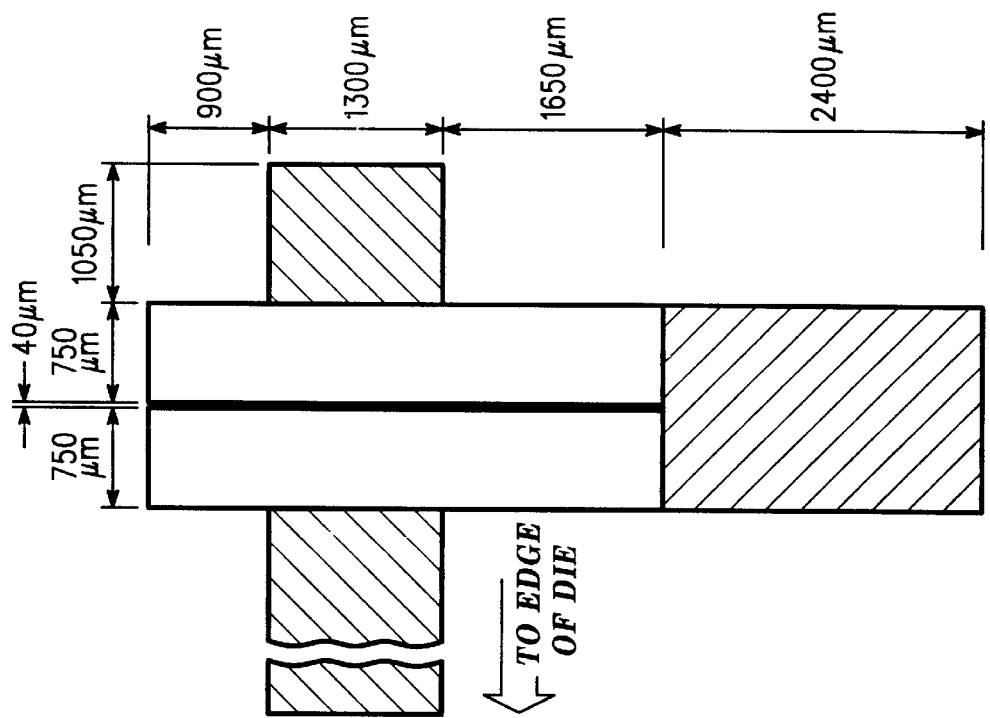
FIGS. 8A–C are slot line designs for a MMIC in a microfluidic device in accordance with embodiments of the present invention.
Figure 8A:
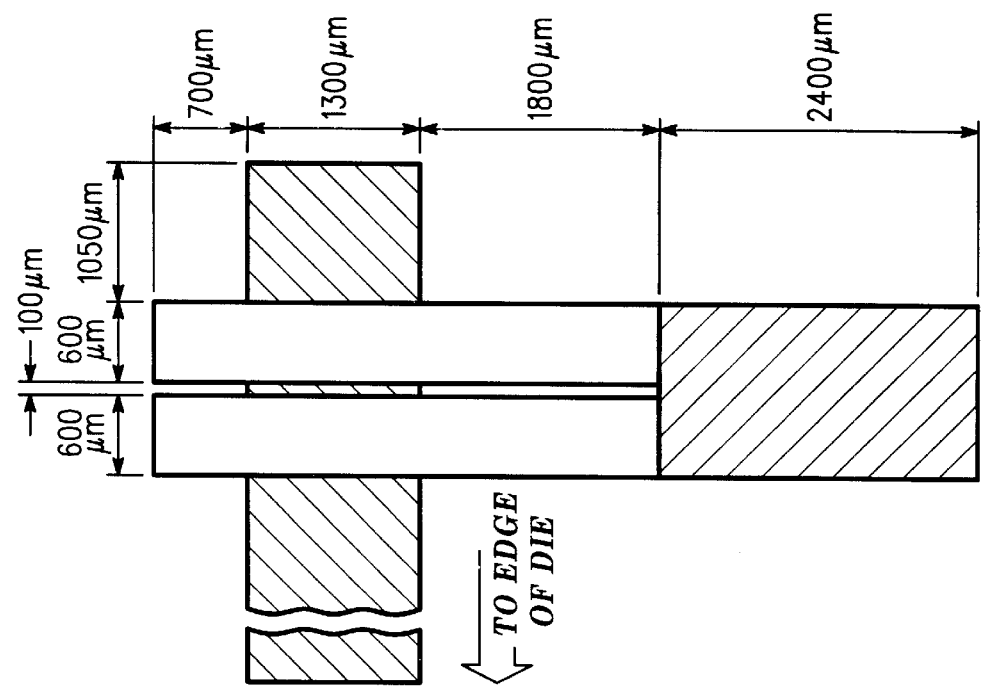
Figure 8C:
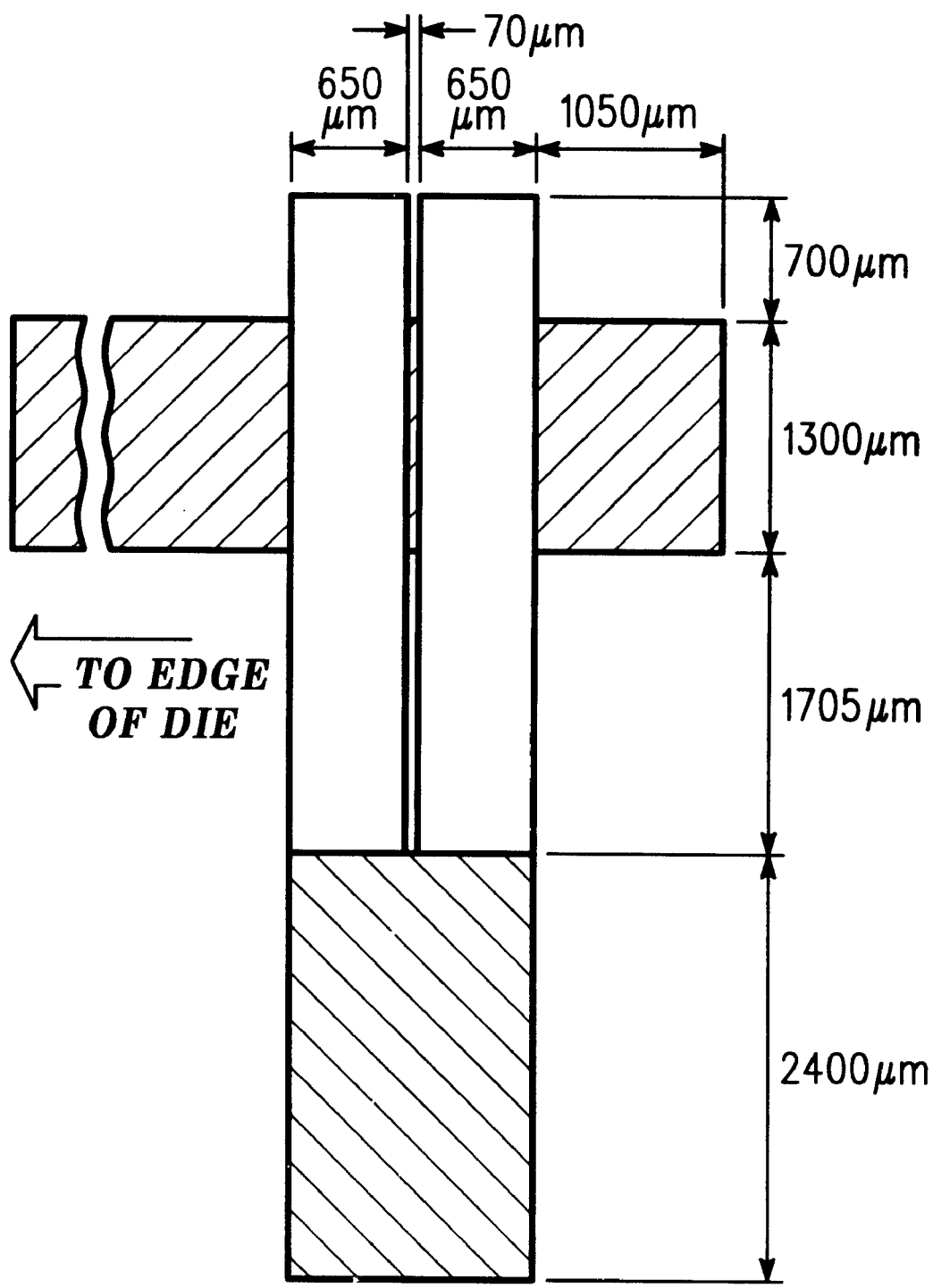
Figure 9:
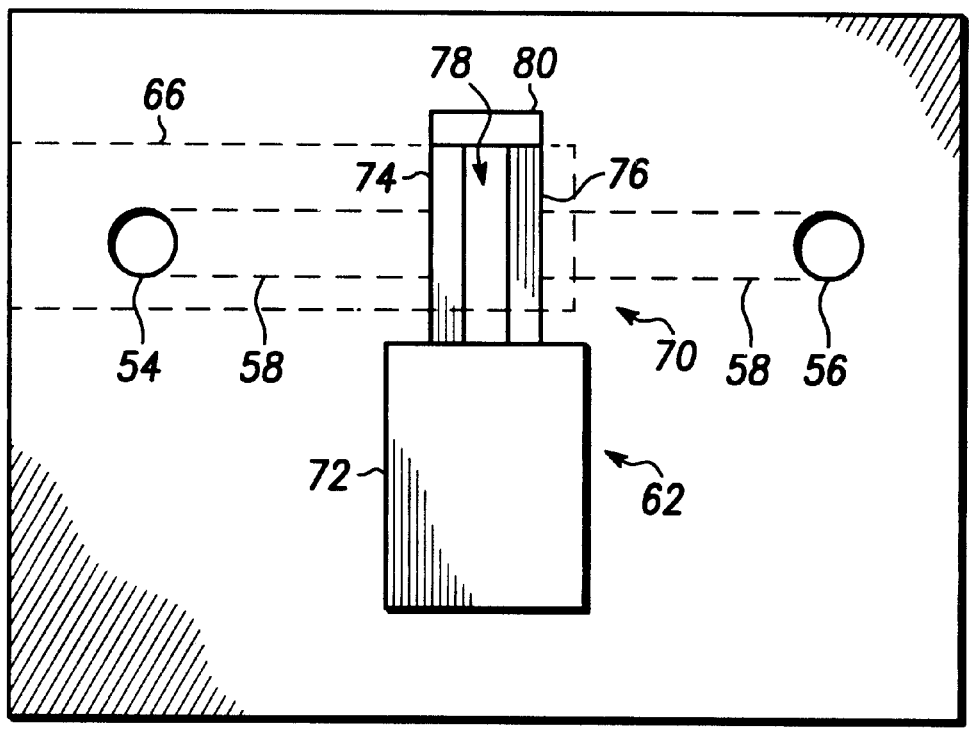
FIG. 9 is a plan-view of an alternative embodiment of the device of FIG. 2.

Referring to FIGS. 5–7, an alternative embodiment of the present invention is depicted. Except for the configuration of the top and bottom conductors of the MMIC, the design of device 42 is generally similar to that of device 10 described above. In particular, device 42 includes a top substrate 44 and bottom substrate 46, which are joined together via an amorphous silicon layer 48 and an insulating layer 50 to form an integrated body. Microfluidic device 42 also includes chamber 52, inlet port 54, outlet port 56, and channels 58. Top conductor 62, formed on top substrate 44, and a bottom conductor 66, formed on bottom substrate 46, together with the material therebetween define a MMIC.

Figure 10:
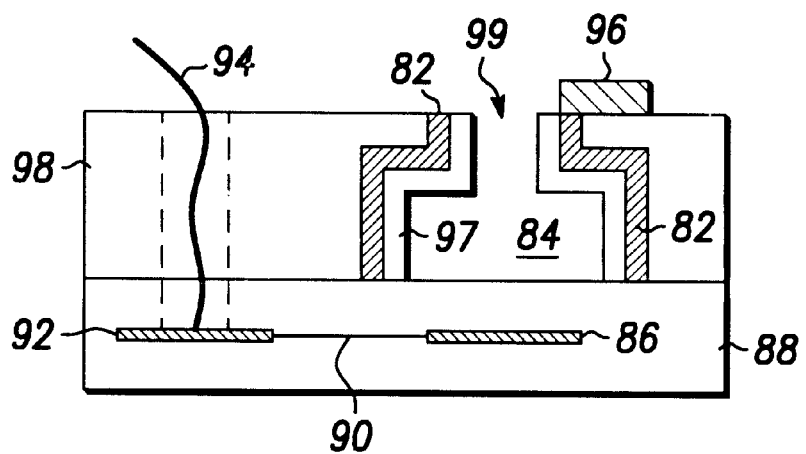
FIG. 10 is a cross-sectional view of a microfluidic device in accordance with an embodiment of the present invention.
Figure 11A:
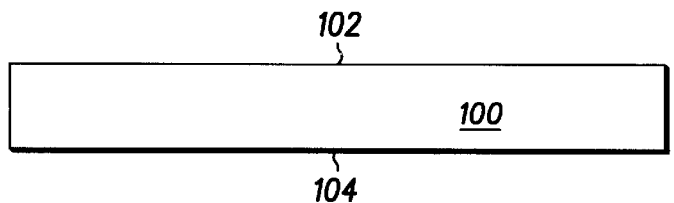
FIGS. 11A–H are cross-sectional schematic views of the structures formed after various steps in the process of fabricating a microfluidic device having a monolithic microwave integrated circuit, in accordance with a preferred embodiment of the present invention.
Figure 11B:
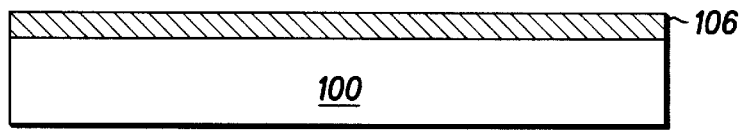
Figure 11C:
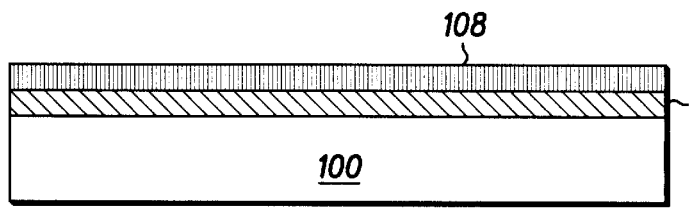
Figure 11D:
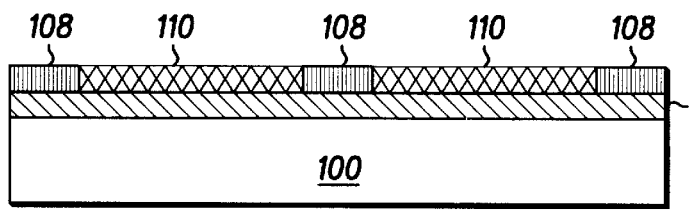
Figure 11E:
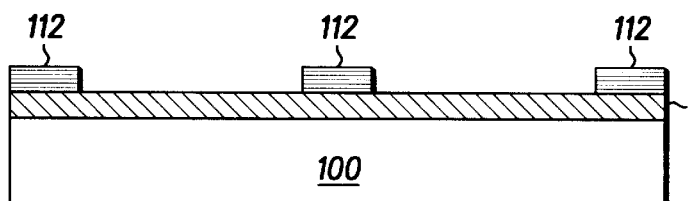
Figure 11F:
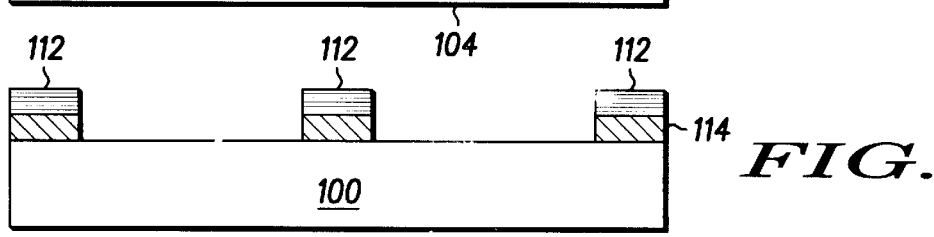
Figure 11G:
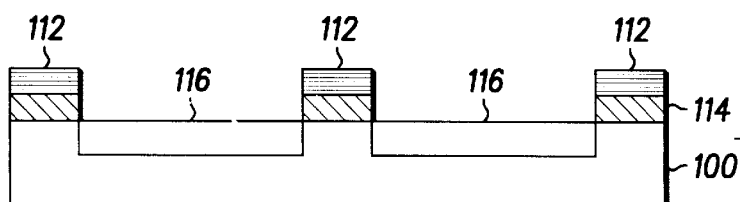
Figure 11H:
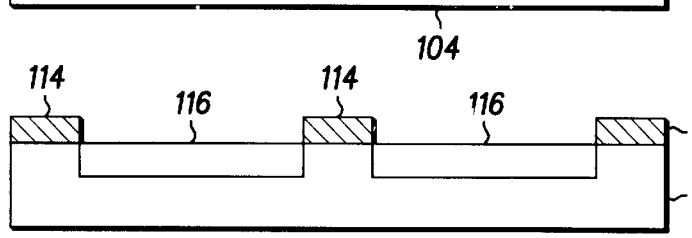
Figure 13A:
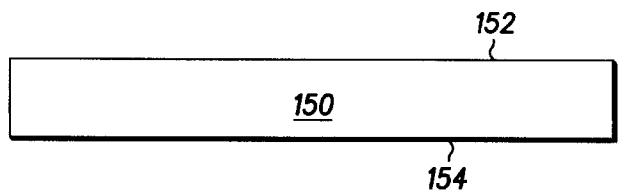
FIGS. 13A–E are cross-sectional schematic views of the structures formed after various steps in the process of fabricating a microfluidic device having a monolithic microwave integrated circuit, in accordance with a preferred embodiment of the present invention.
Figure 13B:
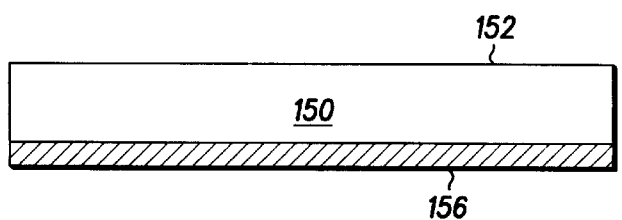
Figure 13C:
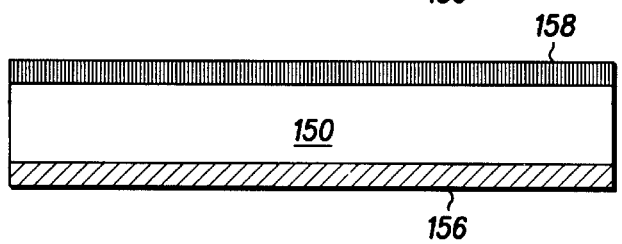
Figure 13D:
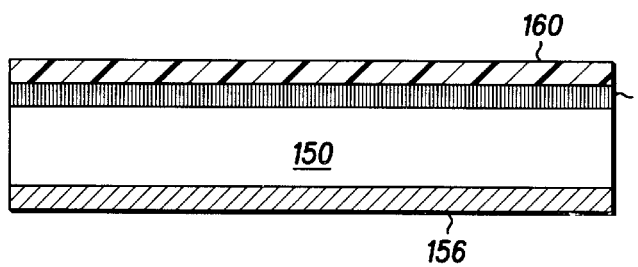
Figure 13E:
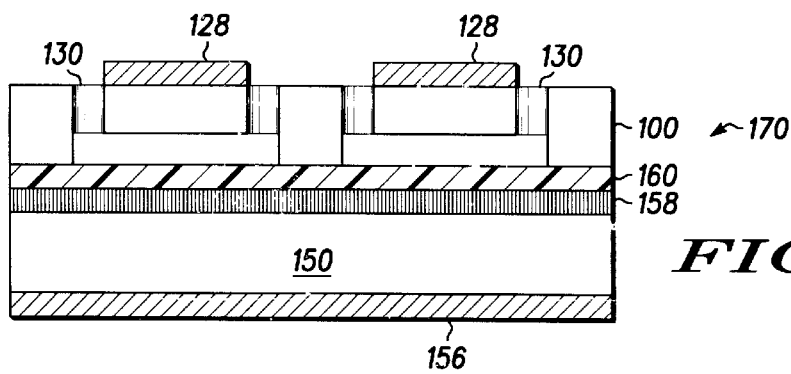
Figure 14A:
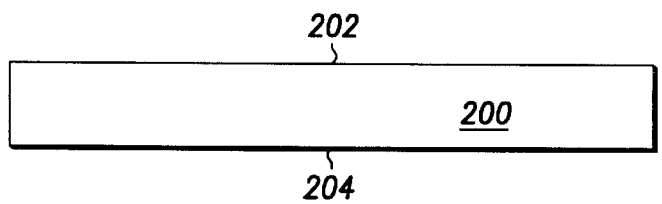
FIGS. 14A–F are cross-sectional schematic views of the structures formed after various steps in the process of fabricating a microfluidic device having a monolithic microwave integrated circuit, in accordance with a preferred embodiment of the present invention.
Figure 14B:
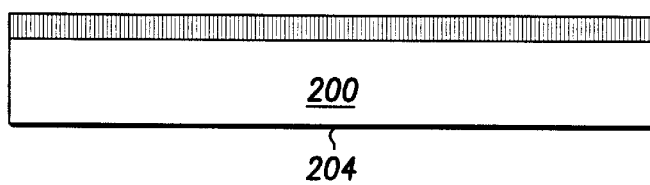
Figure 14C:
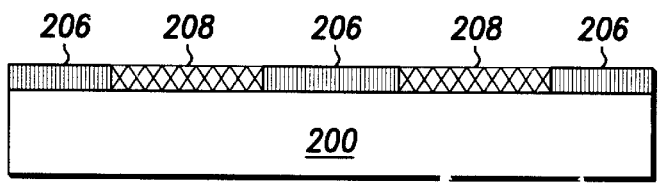
Figure 14D:
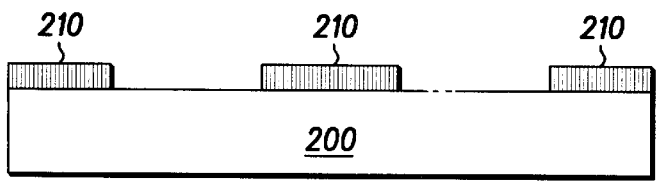
Figure 14E:
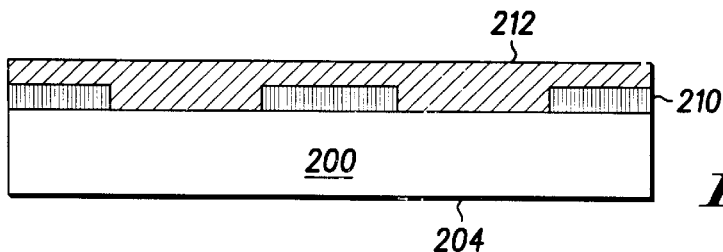
Figure 14F:
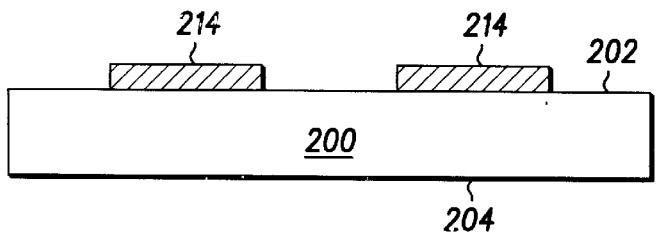
Figure 15A:
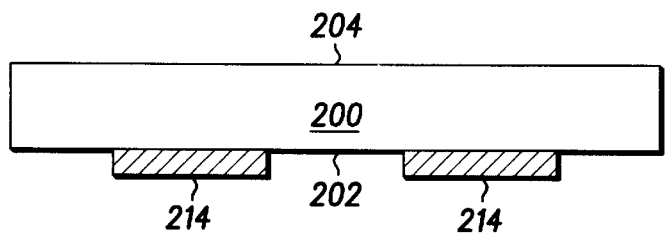
FIGS. 15A–D are cross-sectional schematic views of the structures formed after various steps in the process of fabricating a microfluidic device having a monolithic microwave integrated circuit, in accordance with a preferred embodiment of the present invention.
Figure 15B:
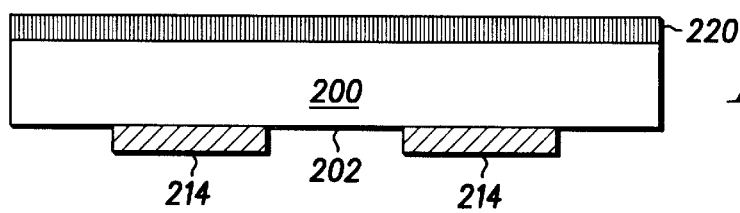
Figure 15C:
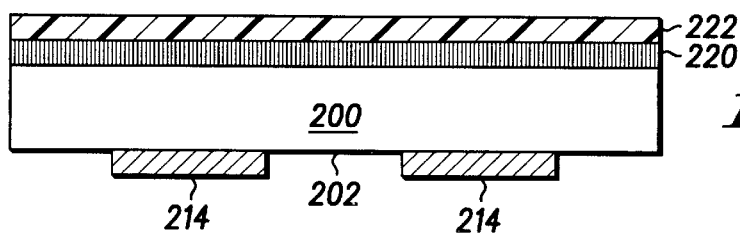
Figure 15D:
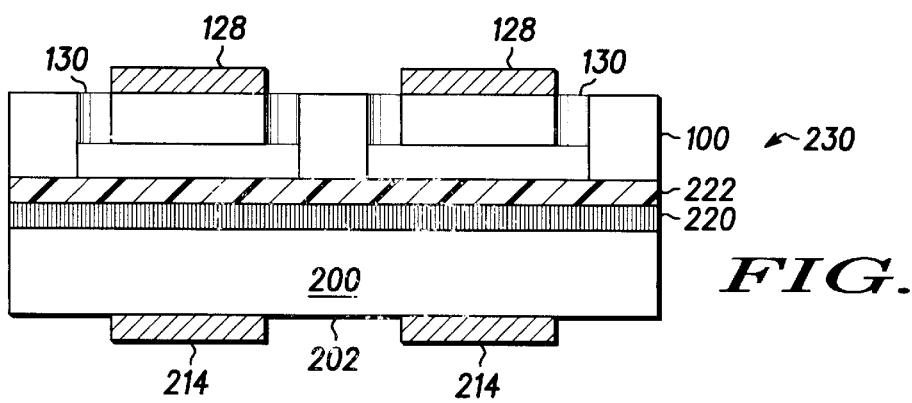

Top conductor 62 has a first portion 70 and a second portion 72. First portion 70 is defined by fingers 74 and 76 and slot 78 therebetween. Slot 78 may be open, as shown in FIG. 5, or closed by section 80, as shown in FIG. 10. Bottom conductor 66 is typically a strip conductor that is arranged to be substantially perpendicular to top conductor 62 and to underlie first portion 70. The microwave feed (not shown) is connected to bottom conductor 66, which extends beyond fingers 74 and 76 approximating an open circuit. The mcirowave energy is coupled to the cavity through the substrate. Preferably, the dimensions of fingers 74, 76 and slot 78 (and portion 80, if present) are approximately the same as underlying chamber 52. The dimensions of second portion 72 are selected to obtain the desired impedance, as described above.

Referring to FIGS. 8A–D, four slot conductor designs were manufactured with the dimensions shown. A microwave source (not shown) was connected to the bottom substrate and coupled to the top substrate. It was found (data not shown) that the devices heated water to a sufficient degree such that it is believed that devices with the depicted designs can be used for applying microwave radiation to a sample within a microfluidic device, an in particular for accomplishing cell lysis and other heating applications within a microfluidic device.

In an alternative embodiment of the present invention, referring to FIG. 10, top conductor 82 lines the ceiling of chamber 84 and bottom conductor 86 is embedded in bottom substrate 88. Contact 90 is also embedded in bottom substrate 88, which is connected to contact pad 92. Probe 94 is in contact with contact pad 92, thereby providing a connection to bottom conductor 86. Top conductor 82 has pad 96 exiting from the top of top substrate 98, thereby providing a connection to top conductor 82. Sample input port is defined by hole 99. Preferably passivation layer 97 (e.g., TEOS) overlies the material of top conductor 82 to provide a relatively non-reactive surface exposed to the sample.

As will be appreciated by the skilled artisan, all of the MMICs described herein have a microwave source connected thereto. Preferably, an amplifier and/or coupler is connected between the microwave source and the MMIC in a manner known to the skilled artisan. Additionally, a computer or on-chip CPU is preferably used to monitor the parameters (such as temperature) in the chamber and control the microwave source and amplifier to achieve predetermined parameters for the chamber.

The present invention also provides microfabrication processes for making microfluidic devices that include MMICs.

As used herein, "microfabrication" refers to processes and techniques for forming microscale components, features, and structures, such as processes used for batch production of semiconductor microelectronic devices. Microfabrication technologies include, but are not limited to, sputtering, electrodeposition, low-pressure vapor deposition, photolithography and etching.

The devices of the invention can be made in a variety of ways, as will be appreciated by those in the art. See for example WO96/39260, directed to the formation of fluid-tight electrical conduits;

U.S. Pat. No. 5,747,169, directed to sealing; EP 0637996 B1; EP 0637998 B1; WO96/39260; WO97/16835; WO98/13683; WO97/16561; WO97/43629; WO96/39252; WO96/15576; WO96/15450; WO97/37755; and WO97/27324; and U.S. Pat. Nos. 5,304,487; 5,071531; 5,061,336; 5,747,169; 5,296,375; 5,110,745; 5,587,128; 5,498,392; 5,643,738; 5,750,015; 5,726,026; 5,35,358; 5,126,022; 5,770,029; 5,631,337; 5,569,364; 5,135,627; 5,632,876; 5,593,838; 5,585,069; 5,637,469; 5,486,335; 5,755,942; 5,681,484; and 5,603,351, all of which are hereby incorporated by reference. Suitable fabrication techniques again will depend on the choice of substrate, but preferred methods include, but are not limited to, a variety of micromachining and microfabrication techniques, including film deposition processes such as spin coating, chemical vapor deposition, laser fabrication, photolithographic and other etching techniques using either wet chemical processes or plasma processes, embossing, injection molding and bonding techniques (see U.S. Pat. No. 5,747,169, hereby incorporated by reference). In addition, there are printing techniques for the creation of desired fluid guiding pathways; that is, patterns of printed material can permit directional fluid transport. Thus, the build-up of "ink" can serve to define a flow channel. In addition, the use of different "inks" or "pastes" can allow different portions of the pathways having different flow properties. For example, materials can be used to change solute/solvent RF values (the ratio of the distance moved by a particular solute to that moved by a solvent front). For example, printed fluid guiding pathways can be manufactured with a printed layer or layers comprised of two different materials, providing different rates of fluid transport. Multi-material fluid guiding pathways can be used when it is desirable to modify retention times of reagents in fluid guiding pathways. Furthermore, printed fluid guiding pathways can also provide regions containing reagent substances, by including the reagents in the "inks" or by a subsequent printing step. See for example U.S. Pat. No. 5,795,453, herein incorporated by reference in its entirety.

As used herein, the terms "photoresist" and "resist" refer to chemical preparations whose solubility in a given fluid is altered by the application of UV light, or other radiation. Photoresists are used to form patterns on a substrate.

As used herein, the term "photomask" refers to a patterned layer of opaque material positioned over a layer of photoresist to create the same pattern or a negative of the pattern in the photoresist by blocking the transmission of UV light, or other radiation, into the photoresist in a pattern corresponding to the pattern of the photomask.

As used herein, the term "planarizing" refers to the process of smoothing steps on a material or substrate layer, wherein the resulting smooth surface is substantially planar. In reference to a material, the term "planarizing" refers to the ability of the material to smooth a stepped surface thereby forming a second substantially planar surface. Conversely, "conformal deposition" refers to the process of smoothing steps on a contoured material or substrate surface while retaining the general contour of the surface.

As used herein, the term "metallization" refers to the process of depositing a layer of metal on a surface of a component of the microfluidic device.

As used herein, the term "anodic bonding" refers to the use of heat and/or electrostatic forces to form an airtight seal between two dissimilar materials.

As used herein, the terms "deposited" or "depositing" generically refer to the process of forming a layer of material on a surface. Specifically, deposition processes include, but are not limited to, vapor deposition, chemical vapor deposition, plasma enhanced chemical vapor deposition, electron beam evaporation, thermal evaporation, sputtering, electroplating and spin coating.

The microfluidic devices may be fabricated in a wide variety of different forms. Many microfluidic devices may be manufactured on a single substrate and can be run in parallel, allowing the processing and analysis of several samples and controls simultaneously. Individual small and disposable dies, each a complete microfluidic device with MMIC, may be fabricated. The device may be fabricated to allow a continual flow of samples through the instrument.

As described above, the body of the device is generally fabricated using one or more of a variety of methods and materials suitable for microfabrication techniques. For example, in preferred aspects, the body of the device may comprise a number of planar members that may individually be injection molded parts fabricated from a variety of polymeric materials, or may be silicon, glass, ceramic or the like. In the case of substrates like silica, glass or silicon, methods for etching, milling, drilling, etc., may be used to produce wells and depressions that make up the various reaction chambers and fluid channels within the device. Microfabrication techniques, such as those regularly used in the semiconductor and microelectronics industries are particularly suited to these materials and methods. These techniques include, e.g., electrodeposition,-low-pressure vapor deposition, photolithography, wet chemical etching, reactive ion etching (RIE), laser drilling, and the like. Where these methods are used, it will generally be desirable to fabricate the planar members of the device from materials similar to those used in the semiconductor industry, i.e., silica, silicon, gallium arsenide, polyimide substrates. U.S. Pat. No. 5,252,294, incorporated herein by reference in its entirety for all purposes, reports the fabrication of a silicon based multiwell apparatus for sample handling in biotechnology applications.

Photolithographic methods of etching substrates are particularly well suited for the microfabrication of these substrates and are well known in the art. For example, the first sheet of a substrate may be overlaid with a photoresist. Radiation may be applied through a photolithographic mask to expose the photoresist in a pattern which reflects the pattern of chambers and/or channels on the surface of the sheet. After removing the exposed photoresist, the exposed substrate may be etched to produce the desired wells and channels. Generally preferred photoresists include those used extensively in the semi-conductor industry. Such materials include polymethyl methacrylate (PMMA) and its derivatives, and electron beam resists such as poly(olefin sulfones) and the like (more fully discussed in, e.g., Ghandi, "VLSI Fabrication Principles," Wiley (1983) Chapter 10, incorporated herein by reference in its entirety for all purposes).

As an example, the wells manufactured into the surface of one planar member make up the various chambers of the device. Channels manufactured into the surface of this or another planar member make up fluid channels, which may be used to fluidly connect the various reaction chambers. Another planar member is then placed over and bonded to the first, whereby the wells in the first planar member define cavities within the body of the device which cavities are the various reaction chambers of the device. Similarly, fluid channels manufactured in the surface of one planar member, when covered with a second planar member define fluid passages through the body of the device. These planar members are bonded together or laminated to produce a fluid tight body of the device. Bonding of the planar members of the device may generally be carried out using a variety of methods known in the art and which may vary depending upon the materials used. For example, adhesives may generally be used to bond the planar members together. Where the planar members are, e.g., glass, silicon or combinations thereof, thermal bonding, anodic/electrostatic or silicon fusion bonding methods may be applied. For polymeric parts, a similar variety of methods may be employed in coupling substrate parts together, e.g., heat with pressure, solvent based bonding. Generally, acoustic welding techniques are generally preferred. In a related aspect, these adhesive tapes may be employed as one portion of the device forming a thin wall of the reaction chamber/channel structures.

Of course, the particular fabrication process and sequence used will depend on the desired characteristics of the device. The skilled artisan may choose from among a wide variety of devices and circuits to implement a desired MMIC feature.

Preferred embodiments of the inventive process provided herewith for fabricating the microfluidic devices with microstrip and slot line MMIC designs are illustrated in FIGS. 10–14.

FIGS. 11A–H show the first steps in the fabrication process for preparing a top substrate 100. Top substrate 100, which has a first surface 102 and a second surface 104, is preferably composed of glass, plastic or silicon. Glass and plastic are particularly preferred for their low cost compared to silicon. Glass is especially preferred. Accordingly, the process steps described herein are the steps that are appropriate when the top substrate is made of glass. However, those skilled in the art would be able to apply corresponding processing steps when top substrate is made of other materials.

Preferably, top substrate 100 is circular and has a diameter preferably of about 75 millimeters to about 300 millimeters.

Preferably, top substrate 100 has a thickness from about 0.5 to about 10 millimeters, more preferably from about 0.5 to 5 millimeters, and most preferably about 1 millimeter. Top substrate 100, however, is not limited to a specific geometry, but may include additional configurations, including rectangular substrates. Those of skill in the art will recognize the applicability of the methods of the present invention to a variety of substrate geometries.

Top substrate 100 is typically cleaned to prepare it for the desired processing steps. In a preferred cleaning process, top substrate 100 is placed in a container with a freshly prepared cleaning solution comprising equal parts (v:v) ammonium hydroxide ($NH_4OH$) and hydrogen peroxide ($H_2O_2$). Heat and mechanical vibration are then applied to clean top substrate 100. For example, substrate 100, in the cleaning solution described above, may be placed in a megasonic cleaner, such as those available from CAE Ultrasonics, Jamestown, N.Y.

Following cleaning, top substrate 100 is primed to enhance adhesion of a metal layer that is later applied to surface 102 and to obtain a smooth, uniform coverage of a photoresist layer that is later applied to the metal layer. In the priming step, surface 102 is coated with a primer layer. Suitable primers include acetone, isopropyl alcohol, methyl alcohol, xylene, trichloroethylene and hexamethyldisilazane ("HMDS"). Most preferably, the primer is hexamethyldisilazane. Preferably, priming with HMDS is performed by placing top substrate 100 in a vacuum oven with a container of high vapor pressure liquid HMDS, thereby allowing the vapor to coat surface 100. Most preferably, top substrate 100 is maintained in the vacuum oven for 15 minutes at 150° C. Alternatively, HMDS may be applied by dispensing a predetermined amount of liquid HMDS on surface 102 and then spinning substrate 100 in a spin-coater to spread out the liquid HMDS to a thin uniform coating.

Following priming, a metal layer 106 is applied to surface 102. In a preferred embodiment, metal layer 106 is formed by using electron beam evaporation to deposit 50 nm of chromium, followed by 200 nm of gold. Alternatively, other metals and other metal layer forming techniques could be used.

Metal layer 106 is then coated with a photoresist layer 108. As is well-known in the art, photoresist materials typically have three components: a resin or base material, a photoactive compound, and a solvent that controls the mechanical properties of the photoresist, e.g, maintaining the photoresist in a liquid state. SRP 950 photoresist (available from Shipley Corp., Marlboro, Mass.) is preferred in this step; however, those skilled in the art will recognize that other photoresists having similar physical and chemical properties, such as those available from Hoechst may also be used. Specifically, the photoresist should be selected based on the desired thickness of the photoresist layer 108.

Many different ways for applying the photoresist to form photoresist layer 108 may be used. A preferred application method is spin coating. In this approach, metal layer 106 is spin-coated by mounting top substrate 100 on a vacuum chuck in a spincoater, such as those available from Headway Research, Garland, Tex. The chuck is then rapidly accelerated at a controlled rotation rate up to a maximum rotational speed of preferably 2000–4000 rpm while liquid photoresist is dispensed on top substrate surface 106. In a preferred embodiment, about 100 to 200 milliliters of photoresist SRP 950 are dispensed while the chuck is rotating at about 4000 rpm for approximately 30 seconds.

An exposure pattern 110 for a microfluidic structure to be formed in substrate 100 is produced in photoresist layer 108 using a photomask. Preferably, a photomask is reusable. Photomasks are typically fabricated on various types of glass or fused silica, and preferably have a high degree of optical transparency, a small thermal expansion coefficient, and a highly polished surface that reduces light scattering. The desired pattern is printed on photomask using an opaque material, usually chromium. A mask aligner, such as those available from Karl Suss, Waterbury Center, Vt., is used to align the photomask with the photoresist layer 108. Photoresist layer 108 covered by a photomask is then exposed to radiation, such as a high intensity ultraviolet (UV) light, which alters the solubility of photoresist layer 108, resulting in a transfer of the desired pattern to photoresist layer 108. Preferably the UV light has a wavelength of 325–410 nanometers and an intensity of about 11 mA/cm.

The pattern transferred depends on the type of photoresist used: positive or negative photoresist. When positive photoresist is used, the pattern formed in the photoresist after developing corresponds exactly to the image on the photomask; negative photoresist responds in the opposite manner, i. e., unexposed regions of the negative resist will dissolve in the developer while exposed regions remain behind. Because positive resist dissolves more quickly during the development process and has better resolution, it is used more widely; however, both positive and negative photoresist patterns fall within the scope of the present invention, and the choice thereof is made according to the understanding of those having skill in the art.

After UV light exposure, photoresist layer 108 is developed to remove excess resist, completing the photolithography process and prepare the substrate for etching. Most preferably, a resist developer, such as MF327, available from Hoechst, is used to remove excess resist. In the case of positive photoresists, exposed regions 110 are removed in this process, leaving behind a patterned photoresist layer 112. After removal of excess photoresist, top substrate 100 is cleaned using oxygen plasma in a plasma etcher, such as the Branson IPC Asher/Etcher available from Branson.

After cleaning, metal layer 106 is etched. In a preferred embodiment of the present invention, metal layer 106 is etched in chromium etchant (such as CR-14 available from Transene, Co., Inc., Danvers, Mass.) and gold etchant (such as KI solution available from Transene Co., Inc.) until the resulting metal pattern 114 is clearly visible on surface 102 of top substrate 100.

Metal pattern 114, in turn, acts as a mask for subsequent etching of a microfluidic pattern 116 into top substrate 100. If top substrate 100 is glass, then a solution of hydrofluoric acid and water (1:1, v/v) may be used for etching. This aqueous chemical etch of concentrated hydrofluoric acid is used to produce cavities with defined side walls and uniform depth. Etch rates are estimated using test wafers, with the final etch typically giving cavities depths of 20 to 100 $\mu$m. For each wafer, the depth of the finished cavity is determined using a surface profilometer.

When top substrate 100 is made out of other materials, other methods for etching may be used. For example, for silicon substrates, "wet" etchants may be used. Such wet etchants include aqueous solutions of "HNA" (a mixture of HF, HNO3, and acetic acid), alkali hydroxides, ammonium hydroxide, tetramethyl ammonium hydroxide, and ethylene diamine pyrochatecol. Alternatively, silicon substrates may be patterned using reactive ion etching (RIE), such as is used for fabricating integrated circuits.

A stripping solution (such as EMT-400, available from EMT Division Brent America, Inc., Campbell, Calif.) is then used to remove the remaining photoresist material, i.e., patterned photoresist layer 112.

In the next steps, which are illustrated in FIGS. 12A–H, the top conductor of the MMIC is formed on top substrate 100. In preferred embodiments, the desired configuration of this top conductor may correspond to a microstrip design or to a slot design, as described above.

In a preferred embodiment of the inventive method, photolithography is used to pattern this top conductor. Thus, as shown in FIGS. 12A–H, a photoresist layer 120 is first applied to surface 104 of top substrate 100. AZ 6210 photoresist (available from AZ Electronic Materials, Somerville, N.J.) is preferred in this step; however, those skilled in the art will recognize that other photoresists having similar physical and chemical properties, such as those available from Shipley and Hitachi, may also be used. Specifically, the photoresist should be selected based on the desired thickness of the photoresist layer 120.

Photoresist layer 120 is then exposed to radiation, such as UV light, applied through a mask, so that exposed regions 122 are formed in photoresist layer 120. A developer is then used to remove exposed regions 122, thereby resulting in a patterned photoresist layer 124. For this process, resist developer AZ 527 is used. However, other developers could also be used, depending on the type of the photoresist used.

Following photolithography, top substrate 100 is cleaned using oxygen plasma in a plasma etcher such as a Branson IPC Asher/Etcher. Evaporation or sputtering is then used to deposit a conductive metal layer 126 overlaying patterned photoresist layer 124 and surface 104 of top substrate 100. To be useful as an interconnect, the metal in layer 126 must have a low resistance to minimize voltage drops along the interconnect lines. Because a single level of metal typically does not provide sufficient capability to fully interconnect complex devices, multilevel metallization is often performed. In particularly preferred embodiments of the devices of the invention, conductor layer 126 is formed by multi-level metallization. Specifically, conductor layer 126 is formed by deposition of sequential layers of conductive metal.

To form conductor layer 126 by evaporation, the following process may be used. Top substrate 100 is loaded into a high capacity vacuum chamber that is evacuated during use preferably by either a diffusion pump or a cryopump. The material to be deposited on top substrate 100 is loaded into a crucible, which is heated by means of an embedded resistance heater or an external power supply. The pressure in the chamber is reduced, preferably to about $1 \times 10^{-6}$ torr, causing the atoms of the metal vapor to strike surface 104 to form a film or a layer of conductive material 126. This process is repeated as necessary with additional metals when multilevel metallization is being performed.

An alternative to evaporation for metal film deposition in microelectronic fabrication is sputtering. Sputtered films generally have better step coverage than evaporated films; however, sputtered films have poor liftoff characteristics. When using sputtering to fabricate conductor layer 126, the plasma chamber described above must be arranged so that a high density of ions strikes a target containing the material to be deposited.

After conductor layer 126 is formed, such as by evaporative deposition or deposition by sputtering as described above, the metal overlying the patterned photoresist 124 is lifted off, leaving behind top conductors 128 in the desired configuration on surface 104. The excess metal in layer 126 is lifted off by top substrate 100 in a cleaning compound, preferably acetone, and using a megasonic cleaner to apply agitation. The cleaning compounds removes photoresist 124, thereby causing the metal overlaying it to lift off. In this way, top conductors 128 are left behind on surface 104.

Patterned metal layer 114 is then removed using the following process. Conductors 128 are first covered for protection by a low tack tape, such as is available from Nitto Denko America, Inc., Fremont, Calif. In a preferred embodiment, patterned metal layer 114 is etched away by applying a gold etchant, such as KI solution available from Transene, Co, Inc., and a chromium etchant, such as is available from Transene Co., Inc. The low tack tape is then removed to expose conductors 128.

The microfabrication process of top substrate 100 is completed by forming inletfoutlet holes 130 extending through surface 104 of substrate 100, which provide access to microfluidic structure 116. Holes 130 may be formed by any process useful for the given material of top substrate 100, including, but not limited to, manual punching and drilling, laser drilling and plasma etching. Holes 130 are preferably from about 0.5 to about 5 millimeters, more preferably from about 1 to about 5 millimeters, and most preferably from about 1.5 to about 2 millimeters in diameter to allow for sample passage. In preferred embodiments, holes 130 are formed by laser drilling.

FIGS. 13A–E shows the preferred steps for processing bottom substrate 150 when a microstrip design of MMIC is used. Bottom substrate 150 is preferably composed of glass, "glass-like", silicon, plastic or a polymeric material. "Glass-like" materials include quartz, sapphire and epitaxial materials. In a particularly preferred embodiment, bottom substrate 150 is composed of glass.

As shown in FIGS. 13A–E, bottom substrate 150 has a first surface 152 and a second surface 154. In the first processing step, a conductive metal layer 156 is deposited on surface 154 to define the bottom conductor. In particularly preferred embodiments of the devices of the invention, conductor layer 156 is formed by multi-level metallization. Specifically, conductor layer 156 is formed by deposition of sequential layers of conductive metal as described above.

Next, an amorphous-silicon layer 158 is deposited on surface 152. Amorphous silicon layer 158 may be applied by sputtering silicon, such as from an MRC sputtering system. Alternatively, amorphous silicon layer 158 may be applied using a plasma enhanced chemical vapor deposition (PECVD) unit, such as available from Novellus Systems, Inc., San Jose, Calif.

An insulating layer 160 is next deposited on amorphous silicon layer 158. When insulating layer 160 is TEOS, the insulating layer is preferably deposited by plasma enhanced chemical vapor deposition (PECVD), such as by using a Novellus PECVD unit Finally, bottom substrate 150 is affixed to top substrate 100 by bonding insulating layer 106 to surface 102 of top substrate 100. In preferred embodiments, anodic bonding is used. In the anodic bonding process, top substrate 100 is placed on top of bottom substrate 150, and substrates 100 and 150 are heated to an elevated temperature, such as approximately 450° C., at which temperature sodium ions in the glass become mobile. While the substrates are at this elevated temperature, a high voltage, typically in the range of about 1000 volts, is then applied between substrates 100 and 150, with top substrate 100 connected to the cathode and bottom substrate 150 connected to the anode. The high voltage causes the formation of a thin layer of silicon dioxide that bonds substrates 100 and 150 together.

With top substrate 100 and bottom substrate 150 bonded together in this way, a microfluidic device 170, having a MMIC in a microstrip design, is provided.

The process for fabricating a microfluidic device having a slot design MMIC is similar. The most significant difference is that in a microstrip design, the bottom conductor need not be patterned, whereas in a slot design, the bottom conductor typically is patterned. FIGS. 14A–F shows preferred steps for patterning a bottom conductor on a bottom substrate 200. As shown in FIGS. 14A–F, bottom substrate 200 has a first surface 202 and a second surface 204, with the bottom conductor to be formed on surface 202.

First, a photoresist layer 206 is applied to surface 202. Photoresist layer 206 is then exposed to radiation, such as UV light, through a mask so that exposed regions 208 are formed therein. A developer is used to remove exposed regions 208, thereby leaving behind a patterned photoresist layer 210 on surface 202 of substrate 200. A conductive metal layer 212 is then formed, such as by evaporation or sputtering as described above, over photoresist layer 210. The portions of layer 212 overlaying photoresist 210 are then lifted off, as described above, leaving behind bottom conductors 214 in the desired configurations on surface 202 of bottom substrate 200.

FIGS. 15A–D shows the subsequent steps used to form the slot design MMIC device. An amorphous silicon layer 220 is formed on surface 204 of bottom substrate 200, and an insulating layer 222, preferably TEOS, is formed on amorphous silicon layer 220, as described above.

Finally, insulating layer 222 is bonded to surface 102 of top substrate 100 (such as by anodic bonding, as described above) to provide a microfluidic device 230 having a slot design MMIC.

The present invention may be used for microwave enhanced biomolecule extraction (particularly nucleic acids) from a microorganism or other cell, in a microfluidic device. Preferably, microwave enhanced nucleic acid extraction is integrated with several other operations all taking place in the same microfluidic device. For illustrative purposes and not by way of limitation, microwave nucleic acid extraction may be integrated with nucleic acid purification, followed by polymerase-chain-reaction amplification. Additionally, a microfluidic device in accordance with an embodiment of the present invention can provide microwave heating for thermocycling during PCR amplification, or other process steps requiring increases in temperature. In this case the substrate, or portion thereof, is preferably made from a material having a relatively high thermal conductivity in contact with a thermal heat sink. Alternatively, or in conjunction with other heat dissipation mechanisms a Peltier thermo electric device may be integrated into the microfluidic device.

Figure 16:
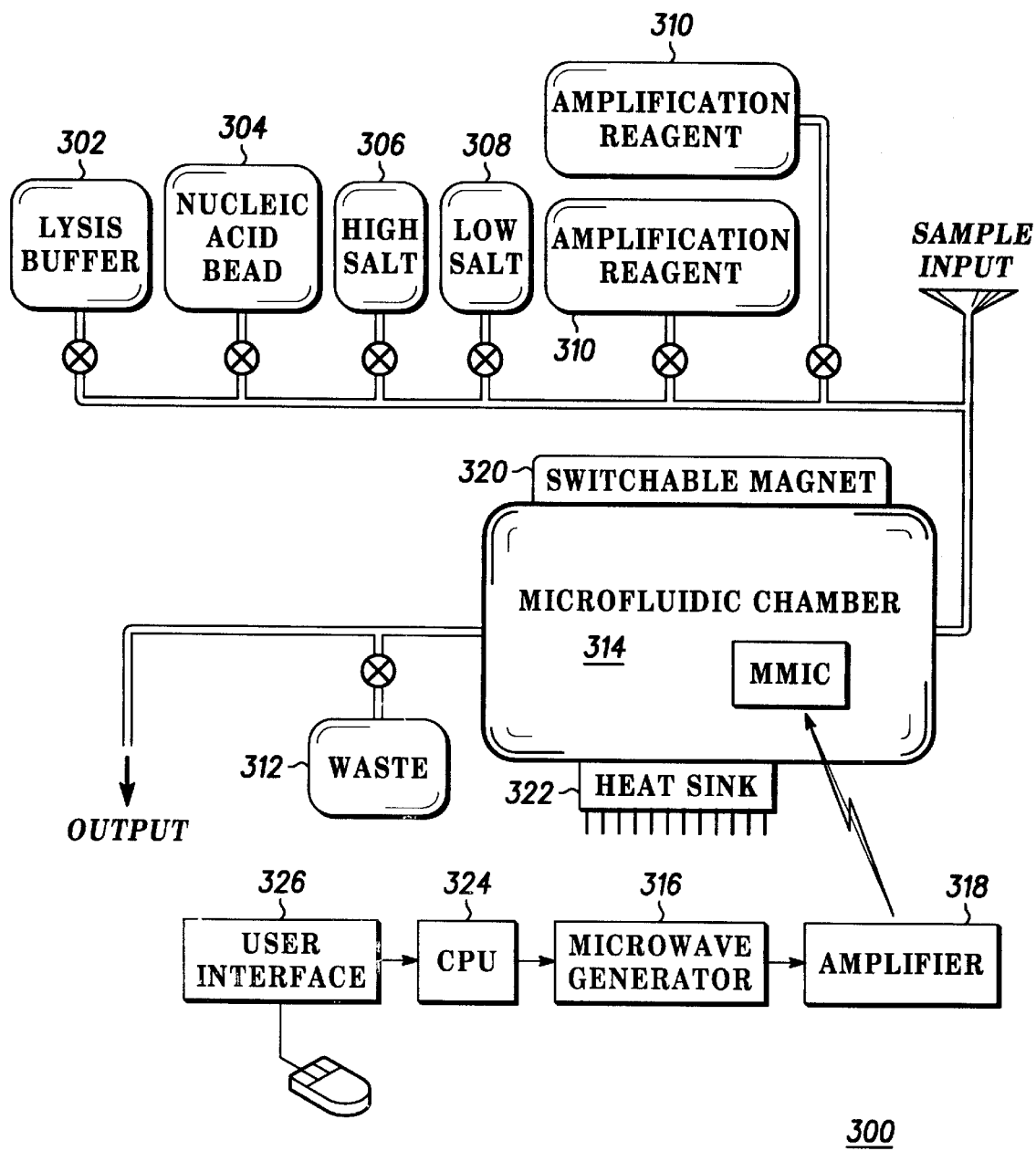
FIG. 16 is a schematic view of an integrated microfluidic system in accordance with an embodiment of the present invention.

Referring to FIG. 16, a system 300 for microwave enhanced nucleic acid extraction from microorganisms in a microfluidic device is depicted. System 300 has lysis buffer reservoir 302, nucleic acid bead reservoir 304, high salt buffer reservoir 306, low salt buffer reservoir 308, amplification reagent reservoirs 310, waste reservoir 312, at least one microfluidic chamber 314 with a MMIC for applying microwave radiation thereto, microwave generator 316, amplifier 318, switchable magnet 320 heat sink 322, CPU or computer controller 324 and user interface 326. It will be appreciated that all of these components may be integrated into the microfluidic device, with the exception of the computer, user interface, microwave generator and amplifier.

The microfluidic system of the present invention has a monolithic microwave integrated circuit (MMIC) for heating and lysing of samples having a volume in picoliter to milliliter scale, more preferably picoliter to less than 100 $\mu$l, and more preferably between approximately 1 nL to 50 $\mu$l. Samples may be less than a milliliter, less than a microliter, less than a nanoliter, or less than a picoliter. It is not intended that the present invention be limited by the nature of the samples heated in the MMIC microfluidic device. For example, samples may be gas, liquid, or solid. Samples include, but are not limited to, chemical and biological samples. Biological samples include, but are not limited to samples from clinical, environmental or forensic testing.

The first step for nucleic acid extraction is introduction of a sample into microfluidic chamber 314. By way of illustration and not limitation, a sample containing bacterial cells in approximately 50 $\mu$L to 100 $\mu$L or less of natural matrix volume (e.g. water, serum, soil, tissue etc.) is introduced into the chamber 314. A volume, approximately equal to the sample volume, of lysis buffer is added to chamber 314 from lysis buffer reservoir 302. The lysis buffer may be introduced from an on-chip storage chamber and an off-chip tank fluidly connected to the device or simply may be present in chamber 314 prior to sample introduction. The composition of the lysis buffer will depend on the starting material, target species, genetic locus, target copy number, etc. Preferably lysis buffer mixtures will contain a minimum of detergent, chelator, pH maintenance and salt components. Additionally, it is preferred not to use an enzymatic digestion step prior to further lytic manipulation, although the device of the present invention is capable of performing this step prior to microwave irradiation.

The sample and lysis buffer are then mixed within the chamber 314. Mixing mechanisms within microfluidic devices are well known in the art.

After the mixing step, microwave radiation is applied to the sample using the MMIC device. The frequency, power, and duration of the radiation will be sufficient to cause degradation of cellular components responsible for cellular integrity. Preferably the times will range between 5–15 seconds for bacteria and 5–10 minutes for eukaryotic cells. However, the skilled artisan will appreciate that the most efficient time will be determined empirically.

The microfluidic device, as described above, is designed to be able to provide accurate temperature control for heating of samples and cell lysis and also to have the flexibility of being able to operate efficiently with a variety of different types of samples. In using the microfluidic device, it is preferable to determine, by means of an input power measuring instrument and an output power measuring instrument, the power loss intrinsic to a microwave chamber, i.e., with no sample present, over the range of available source frequencies. Then, when a sample is added, the power loss can be measured again to determine the absorbance [SP?] of the sample. Based on this absorbance, computer 324 can set the power level of microwave source 316 and/or the gain of an amplifier so that the input power level will be optimal for heating of samples and cell lysis. Alternatively, since nucleic acid extraction seems to be correlated with sample temperature, computer 324 can monitor sample temperature (via thermocouples integrated into the device) and set power and duration levels to achieve and maintain the desired temperature for cell lysis to proceed. For example, a cell lysis operation may require that the sample be maintained at a particular temperature, such as 100° C., for a particular period of time. By monitoring the sample temperature, and by controlling the source power level of a microwave source and/or the gain of an amplifier, computer 324 can control the temperature ramp rate and can maintain the sample temperature at a predetermined level for a predetermined time for optimal cell lysis.

In co-pending and co-assigned U.S. Ser. No. 09/347,691 (filed Sep. 16, 1999), incorporated herein in its entirety by reference, it was found that by using high frequency microwave radiation, the heating of small samples, and, thus, cell lysis in small samples, is much more efficient than using the 2.45 GHz frequency of conventional microwave ovens. Without being bound by any particular theory, it is believed that enhanced heating occurs because the shorter wavelength of the high frequency microwaves are closer to the dimensions of the sample being heated. Additionally, biological samples are composed mostly of water. Thus, as a very good first approximation, a cell sample can be considered as water to establish microwave power, frequency and duration settings to achieve the desired temperature. It is known that pure water has a broad dipole resonance at approximately 21 GHz, depending on the phase, temperature, and the presence of impurities. These empirical results can then be used during the cell lysis procedure to ensure better results.

Thus, the use of microwave radiation in the frequency range of 18 to 26 GHz will be particularly efficient at heating because of this resonant absorption. Referring to FIGS. 4A–C, frequencies between about 21 to about 22 GHZ are particularly preferred. These data are in agreement with the findings disclosed in co-pending U.S. Ser. No. 09/347,691. More specifically, it was found that a frequency range of about 20 to 22 GHZ, and an input power level of approximately 30 dBm (1 Watt) heated a 25 microliter sample of deionized water to its boiling point in approximately 20 seconds. In contrast, it was found that the same amount of sample could not be heated in a conventional microwave oven operating at 2.45 GHZ and a power level of over 600 Watts. Even after 110 seconds of heating the 25 microliter sample using a thermal block, namely a conventional hotplate at a temperature of 120° C., the sample temperature still did not reach 100° C. The results for deionized water were found also to apply to biological samples, indicating that the technique is useful for heating biological samples, and microwave cell lysis in particular. It was found that a frequency of approximately 22 GHZ and a power level of approximately 29.7 dBm heated a 25 microliter sample of *E. coli* from room temperature to 100° C. in about 20 seconds.

In addition to the resonance at approximately 21 GHZ, water has other higher frequency resonances. For example, water vapor also has resonances at approximately 190 GHZ and at approximately 310 GHZ. The MMIC approach of the present invention may be used for these 190 GHZ and 310 GHZ resonances, though much smaller dimensions would be required.

Following microwave enhanced lysis, the nucleic acid is removed from the lysate. Preferably, the lysate is contacted with magnetic polymer micro-beads (e.g., DNA Direct™ from Dynal, Inc.), the material of which absorbs nucleic acid at high salt concentrations (e.g., 3–4M Na$^+$). The beads are preferably delivered into the chamber 314 from bead reservoir 304. Alternatively, the lysate is transported into an on-chip bead chamber under high salt conditions. As previously discussed the bead and salt solutions may be on-chip or off-chip. Alternatively, the lysing chamber may be coated with the nucleic acid absorbing materials, or a channel may be packed with the beads or lined with the material thereof to form a column from which nucleic acid would be extracted from the lysate flowing therethrough. Although the buffer supplied by Dynal, Inc. is proprietary, the ionic conditions promoting nucleic acid adsorption are well know in the art. See, e.g., Vogelstein & Gillespie (1979).

The DNA Direct™ beads are supplied as a suspension of approximately 5×10$^8$ beads/mL. Approximately 200 µL of beads will bind 200 ng of DNA, or 1 ng/µL of beads. Hence, it is possible for the skilled artisan to introduce the appropriate volume of bead solution depending on the anticipated recovery of nucleic acid from a particular sample (if known). With the exception of the small animal virus and bacteriophage genomes, all biological sample types theoretically yield recoverable amounts of genetic material from single cells or virus particles using the preferred magnetic bead technology.

After introducing the beads, the resulting mixture is mixed. Preferably, an alternating magnetic field is applied to chamber 314 by on-chip switchable magnet 329 resulting in the mixing. It is well known in the art how to integrate a circuit in a microfluidic device for generating and applying an alternating magnetic field. Incubation times and temperature for optimal adsorption can be determined empirically. The MMIC can be used to achieve the desired temperatures, as previously described.

After incubation, the magnetic beads containing the adsorbed nucleic acid are immobilized on the inner wall of chamber 314 by applying a magnetic field from switchable magnet 320. The unbound cellular debris, sample matrix material and other cellular/sample components are flushed out of the chamber with a high salt wash buffer under high salt conditions (e.g., 3–4M Na+) from high salt buffer reservoir 306. Under these conditions the nucleic acid will remain associated with the immobilized magnetic beads within the chamber. The cellular debris and other waste can be collected in waste reservoir 312 for further analysis or disposal.

Following the high-salt wash step, the magnetically immobilized beads containing the adsorbed nucleic acid are washed with a low salt (e.g., 10 mM Na$^+$) elution buffer from low salt buffer reservoir 308. Under low salt concentration, the nucleic acid is eluted from the polymer surface of the beads into solution. Mixing may be done to facilitate the elution process. The elution process preferably takes place in chamber 314, but as with other steps it may be done in a cavity separate from chamber 314.

Following elution from the beads, the nucleic acid may undergo any number of different microbiologic processes, such as and without limitation, PCR amplification, spectrophotometric quantification, labeling, or application to an oligonucleotide-probe array for taxonomic or diagnostic analysis. All of these operations can be integrated into the microfluidic device of the present invention.

In a preferred embodiment the nucleic acid is amplified by PCR. The microfluidic device of the present invention is particularly suited for this by virtue of its ability to locally apply microwave radiation to heat the sample. This is a large advantage over heating by embedded resistive heaters or by thermocycling the entire device because microwave radiation heats more uniformly, and heating is discontinued immediately upon cessation of radiation. Other suitable target amplification techniques include, but are not limited to, strand displacement amplification (SDA), and nucleic acid sequence based amplification (NASBA).

In a preferred embodiment, the target amplification technique is PCR. The polymerase chain reaction (PCR) is widely used and described, and involves the use of primer extension combined with thermal cycling to amplify a target sequence; see U.S. Pat. Nos. 4,683,195 and 4,683,202, and PCR Essential Data, J. W. Wiley & sons, Ed. C. R. Newton, 1995, all of which are incorporated by reference. In addition, there are a number of variations of PCR which also find use in the invention, including "quantitative competitive PCR" or "QC-PCR", "arbitrarily primed PCR" or "AP-PCR", "immuno-PCR", "Alu-PCR", "PCR single strand conformational polymorphism" or "PCR-SSCP", "reverse transcriptase PCR" or "RT-PCR", "biotin capture PCR", "vectorette PCR", "panhandle PCR", and "PCR select cDNA subtraction", among others. In one embodiment, the amplification technique is not PCR.

In general, PCR may be briefly described as follows. The purified nucleic acid in chamber 314 is denatured, by applying microwave radiation from the MMIC to raise the temperature, and then cooled in the presence of an excess of a PCR primer, which then hybridizes to the first target strand. The PCR primer and other necessary PCR reagents are added to chamber 314 from PCR reagent reservoir 310. Alternatively, the purified nucleic acid sample may be transferred into a different on-chip cavity containing the necessary PCR reagents. Cooling takes place by incorporating thermally conductive probes or surfaces within the chamber, which are connected to thermal heat sink 322. A DNA polymerase then acts to extend the primer, resulting in the synthesis of a new strand forming a hybridization complex. The sample is then heated again, to disassociate the hybridization complex, and the process is repeated. By using a second PCR primer for the complementary target strand, rapid and exponential amplification occurs. Thus PCR steps are denaturation, annealing and extension. The particulars of PCR are well known, and include the use of a thermostable polymerase such as Taq I polymerase and thermal cycling. In accordance with an embodiment of the present invention, computer 324 monitors and controls the thermocycling by controlling the application of microwave radiation to the sample.

All reagents, as with previously described processes, can be stored on- or off-chip. A series of microfluidic pumps and valves are utilized to introduce, transfer or remove fluids into or out of cavities within the microfluidic device of the present invention.

In certain embodiments of the present invention, fluids (e.g., gases, liquids, samples, reagents and the like) can be deposited in appropriate cavities within the microfluidic device, or can be moved from one cavity to another cavity on the microchip. In preferred embodiments, fluids can be delivered to or through the cavities of the device using a microfluidic reagent distribution system, as outlined herein or as currently known in the art. In preferred embodiments, the microfluidic distribution system is controlled by pressure pumping means, or by electro-osmotic pumping means. Fluid flow is controlled by valving using a system of microfluidic channels and chambers to advantageously direct fluid flow and storage within the device.

In a preferred embodiment, the devices of the invention include at least one fluid pump. Pumps generally fall into two categories: "on chip" and "off chip"; that is the pumps (generally electrode based pumps) can be contained within the device itself, or they can be contained on an apparatus into which the device fits, such that alignment occurs of the required flow channels to allow pumping of fluids.

In a preferred embodiment, the pumps are contained on the device itself. These pumps are generally electrode based pumps; the application of electric fields can be used to move both charged particles and bulk solvent, depending on the composition of the sample and of the device. Suitable on chip pumps include, but are not limited to, electroosmotic (EQ) pumps and electrohydrodynamic (EHD) pumps; these electrode based pumps have sometimes been referred to in the art as "electrokinetic (EK) pumps". All of these pumps rely on configurations of electrodes placed along a flow channel. As is described in the art, the configurations for each of these electrode based pumps are slightly different. For example, in EHD pumps better fluid flow occurs by shortening the distance between electrodes along a channel. In EQ pumps better fluid flow occurs by lengthening th distance between electrodes along the channel.

In a preferred embodiment, an electroosmotic pump is used. Electroosmosis (EQ) is based on the fact that the surface of many solids, including quartz, glass and others, become variously charged, negatively or positively, in the presence of ionic materials. The charged surfaces will attract oppositely charged counterions in aqueous solutions. Applying a voltage results in a migration of the counterions to the oppositely charged electrode, thereby moving the bulk of the fluid as well. The volume flow rate is proportional to the current, and the volume flow generated in the fluid is also proportional to the applied voltage. Electroosmostic flow is useful for liquids having some conductivity, and is generally not applicable for non-polar solvents. EQ pumps are described in U.S. Pat. Nos. 4,908,112 and 5,632,876, PCT US95/14586 and WO97/43629, incorporated by reference.

In a preferred embodiment, an electrohydrodynamic (EHD) pump is used. In EHD pumps electrodes transfer electrical charge to the fluid when a voltage is applied. This charge transfer occurs either by transfer or removal of an electron to or from the fluid, such that liquid flow occurs from the charging electrode to the oppositely charged electrode. EHD pumps can be used to pump resistive fluids such as non-polar solvents. EHD pumps are described in U.S. Pat. No. 5,632,876, hereby incorporated by reference.

The electrodes of the pumps preferably have a diameter from about 25 µm to about 100 µm, more preferably from about 50 µm to about 75 µm. Preferably, the electrodes protrude from the top of a flow channel to a depth of from about 5% to about 95% of the depth of the channel, with from about 25% to about 50% being preferred. In addition, as described in PCT US95/14586, an electrode-based internal pumping system can be integrated into the liquid distribution system of the devices of the invention with flow-rate control at multiple pump sites and with fewer complex electronics if the pumps are operated by applying pulsed voltages across the electrodes; this gives the additional advantage of ease of integration into high density systems, reductions in the amount of electrolysis that occurs at electrodes, reductions in thermal connection near the electrodes, and the ability to use simpler drivers, and the ability to use both simple and complex pulse wave geometries.

The voltages required to be applied to the electrodes cause fluid flow depends on the geometry of the electrodes and the properties of the fluids to be moved. The flow rate of the fluids is a function of the amplitude of the applied voltage between electrode, the electrode geometry and the fluid properties, which can be easily determined for each fluid. Test voltages used may be up to about 1500 volts, but an operating voltage of about 40 to 300 volts is desirable. An analog driver is generally used to vary the voltage applied to the pump from a DC power source. A transfer function for each fluid is determined experimentally as that applied voltage that produces the desired flow or fluid pressure to the fluid being moved in the channel. However, an analog driver is generally required for each pump along the channel and is suitable an operational amplifier.

In an alternative embodiment, an "off-chip" pump is used. For example, the devices of the invention may fit into an apparatus or appliance that has a nesting site for holding the device, that can register the ports (i.e. sample inlet ports, fluid inlet ports, and waste outlet ports) and electrode leads. The apparatus can including pumps that can apply the sample to the device; for example, can force cell-containing samples into the microwave chamber for cell lysis, after which the lysed sample is pumped to another portion of the device for additional process steps. Such pumps are well known in the art.

In a preferred embodiment, the devices of the invention include at least one fluid valve that can control the flow of fluid into or out of a module of the device, or divert the flow into one or more channels. A variety of valves are known in the art. For example, in one embodiment, the valve may comprise a capillary barrier, as generally described in PCT US97/07880, incorporated by reference. In this embodiment, the channel opens into a larger space designed to favor the formation of an energy minimizing liquid surface such as a meniscus at the opening. Preferably, capillary barriers include a dam that raises the vertical height of the channel immediately before the opening into a larger space such a chamber. In addition, as described in U.S. Pat. No. 5,858,195, incorporated herein by reference, a type of "virtual valve" can be used.

The foregoing description, for purposes of explanation, used specific nomenclature to provide a thorough understanding of the invention. Nevertheless, the foregoing descriptions of the preferred embodiments of the present invention are presented for purposes of illustration and description and are not intended to be exhaustive or to limit the invention to the precise forms disclosed; obvious modification and variations are possible in view of the above teachings. Accordingly, it is intended that the scope of the invention be defined by the following claims and their equivalents.

What is claimed is:

1. A method for lysing cells in a cavity of a microfluidic device comprising:

introducing a cell into said cavity;

providing microwave radiation comprising at least one of a predetermined frequency, a predetermined wavelength and a predetermined intensity; and heating said cavity for an effective duration of time with said microwave radiation from a monolithic microwave intograted circuit (MMIC) in order to form a cell lysate, wherein said MMIC is substantially integrated with said microfluidic device.

2. The method according to claim 1, wherein said MMIC comprises microstrip line conductors disposed substantially adjacent to said cavity.

3. The method according to claim 1, wherein said MMIC comprises slot line conductors disposed substantially adjacent to said cavity.

4. The method according to claim 1, wherein said cavity comprises at least one of a fluid chamber and a fluid channel.

5. The method according to claim 1, wherein said cell comprises at least one of a eukaryotic cell, a prokaryotic cell and a mammalian tumor cell.

6. The method according to claim 1, wherein said cavity comprises at least one of an inlet port and an outlet port, said inlet port substantially connected to a plurality of reagent sources; and wherein said microfluidic device is operatively associated with a computer controller for controlling at least one of reagent flow and application of microwave radiation.

7. The method according to claim 6, wherein said MMIC is operatively associated with a microwave generator.

8. The method according to claim 6, wherein said reagent sources are substantially integrated into said microfluidic device.

9. The method according to claim 6, wherein said plurality of reagent sources comprise at least one of lysis buffer, magnetic nucleic acid absorption bead solution, high salt buffer and low salt buffer.

10. A method for lysing viral particles in a cavity of a microfluidic device comprising:

introducing a viral particle into said cavity;

providing microwave radiation comprising at least one of a predetermined frequency, a predetermined wavelength and a predetermined intensity; and heating said cavity for an effective duration of time with said microwave radiation from a monolithic microwave integrated circuit (MMIC) in order to form a viral particle lysate, wherein said MMIC is substantially integrated with said microfluidic device.

* * * * *